United States Patent
Walker et al.

(10) Patent No.: US 11,717,410 B2
(45) Date of Patent: *Aug. 8, 2023

(54) IMPLANTABLE TISSUE REPAIR DEVICES

(71) Applicant: ORTHOX LIMITED, Abingdon (GB)

(72) Inventors: Robert Alan Walker, Abingdon (GB);
Ben Armstrong, Abingdon (GB);
Nicholas James Vavasour Skaer,
Abingdon (GB)

(73) Assignee: ORTHOX LIMITED, Abingdon (GB)

( * ) Notice: Subject to any disclaimer, the term of this patent is extended or adjusted under 35 U.S.C. 154(b) by 20 days.

This patent is subject to a terminal disclaimer.

(21) Appl. No.: 16/615,357

(22) PCT Filed: May 22, 2018

(86) PCT No.: PCT/GB2018/051385
§ 371 (c)(1),
(2) Date: Nov. 20, 2019

(87) PCT Pub. No.: WO2018/215756
PCT Pub. Date: Nov. 29, 2018

(65) Prior Publication Data
US 2020/0155322 A1   May 21, 2020

(30) Foreign Application Priority Data
May 23, 2017 (GB) .................... 1708233

(51) Int. Cl.
*A61F 2/30* (2006.01)
*A61L 27/52* (2006.01)

(52) U.S. Cl.
CPC ...... *A61F 2/30756* (2013.01); *A61F 2/30749* (2013.01); *A61F 2/30965* (2013.01);
(Continued)

(58) Field of Classification Search
CPC .............. A61F 2/30756; A61F 2/30749; A61F 2/30965; A61F 2/3872
See application file for complete search history.

(56) References Cited

U.S. PATENT DOCUMENTS 6,783,554 B2 * 8/2004 Amara ............. A61B 17/12168
606/151
9,498,335 B2 * 11/2016 McCullen ............. A61F 2/3872
(Continued)

FOREIGN PATENT DOCUMENTS

WO   2004/026190 A2   4/2004
WO   2006/060555 A1   6/2006
(Continued)

OTHER PUBLICATIONS

International Search Report for corresponding PCT application No. PCT/GB2018/051385, dated Aug. 22, 2018.
(Continued)

*Primary Examiner* — Marcia L Watkins
(74) *Attorney, Agent, or Firm* — Notaro, Michalos & Zaccaria P.C.

(57) ABSTRACT

An implantable tissue repair device containing a body having a biocompatible hydrogel and a plurality of tissue anchoring elements projecting from the body, where the anchoring elements are integrally formed with the body and have the same biocompatible hydrogel as the body, and the anchoring elements, in use, are arranged to enter apertures in a tissue and anchor the device to the tissue.

13 Claims, 14 Drawing Sheets

(52) U.S. Cl.
CPC ..... *A61L 27/52* (2013.01); *A61F 2002/30062* (2013.01); *A61F 2002/3092* (2013.01); *A61F 2002/30461* (2013.01); *A61F 2002/30878* (2013.01); *A61F 2002/30957* (2013.01)

(56) References Cited

U.S. PATENT DOCUMENTS

| | | | |
|---|---|---|---|
| 10,034,755 B2* | 7/2018 | McCullen | A61F 2/30767 |
| 2002/0173855 A1 | 11/2002 | Mansmann | |
| 2002/0183845 A1 | 12/2002 | Mansmann | |
| 2004/0101518 A1 | 5/2004 | Vacanti | |
| 2005/0287187 A1 | 12/2005 | Mansmann | |
| 2006/0235542 A1 | 10/2006 | Hodorek et al. | |
| 2007/0100450 A1* | 5/2007 | Hodorek | A61L 27/52 623/14.12 |
| 2007/0179607 A1 | 8/2007 | Hodorek et al. | |
| 2007/0179621 A1 | 8/2007 | McClellan et al. | |
| 2007/0224238 A1 | 9/2007 | Mansmann et al. | |
| 2009/0171467 A1* | 7/2009 | Mann | B29C 70/222 623/23.63 |
| 2014/0277451 A1* | 9/2014 | Ganz | A61B 17/562 623/14.12 |
| 2014/0324169 A1 | 10/2014 | Maher et al. | |
| 2015/0105863 A1* | 4/2015 | Zussman | A61L 27/26 623/23.72 |
| 2018/0289493 A1* | 10/2018 | Mansmann | A61F 2/30756 |
| 2020/0069430 A1* | 3/2020 | Walker | A61F 2/441 |
| 2020/0205986 A1* | 7/2020 | Skaer | A61F 2/442 |

FOREIGN PATENT DOCUMENTS

| | | |
|---|---|---|
| WO | 2007020449 A2 | 2/2007 |
| WO | 2009133532 A1 | 11/2009 |
| WO | 2009156760 A2 | 12/2009 |
| WO | 2016112175 A1 | 7/2016 |

OTHER PUBLICATIONS

First Search Report for corresponding GB application No. GB 1708233.0, dated Nov. 8, 2017.
Second Search Report for corresponding GB application No. GB 1708233.0, dated Mar. 9, 2018.

* cited by examiner

IMPLANTABLE TISSUE REPAIR DEVICES

TECHNICAL FIELD OF THE INVENTION

This invention relates to implantable tissue repair devices and methods for manufacturing implantable tissue repair devices. In particular, but not exclusively the invention relates to implantable tissue repair devices with improved means to anchor or secure the devices to, or adjacent to, a tissue in need to repair, such as bone or cartilage.

BACKGROUND TO THE INVENTION

Cartilage in the adult mammalian body occurs in three principal forms: hyaline cartilage; white fibrocartilage; and yellow elastic cartilage. Hyaline cartilage is chiefly present as articular cartilage in the synovial diarthroidal joints e.g. the knee, hip and shoulder, and between long bones, where it forms the stiff and smooth articulating surfaces. White fibrocartilage is present in the menisci of the knee and temporomandibular joint of the jaw and in intervertebral discs. Yellow elastic cartilage gives support to the epiglottis, Eustachian tube and external ear.

Three pathological conditions involving cartilage damage are very common: osteoarthrosis of articular cartilage; injury to the fibrocartilage of the knee menisci; collapse, rupture or herniation of the intervertebral disc; and damage caused by rheumatoid arthritis. Osteoarthrosis is caused by the progressive damage and breakdown of articular cartilage most commonly in the hip and knee and is an important cause of pain and reduced mobility in young and old people alike. Injury to the fibrocartilage of the meniscus is a common sports injury and is also seen as a result of road traffic accidents and other traumatic injuries.

Articular cartilage is highly specialized to provide a relatively frictionless, highly lubricated, wear resistant surface between relatively rigid bones. It also functions to transmit and distribute the forces arising from loaded contact to the surrounding cartilage and underlying subchondral trabecular bone. It is a nonvascular connective tissue largely composed of a fluid phase consisting principally of water and electrolytes interspersed in a solid phase containing type II collagen fibrils, proteo-glycan and other glycoproteins. The latter constituents surround, and are secreted by, highly specialized mesenchymal cells, the chondrocytes, which account for some 10% of the volume of articular cartilage. The collagen fibrils within articular cartilage are arranged in a complex arcade structure forming columns arranged normal to and anchored in the osteochondral junction. These columns run up through the deep layer of cartilage, but the predominant fibre orientation gradually changes to form the arches of the arcade structure in the superficial cartilage. In the superficial layer which abuts the joint space, the meshwork of collagen fibrils is much denser while the fibrils are almost entirely tangential to the cartilage surface. The orientation of collagen in articular cartilage is vital to its mechanical function. Healthy articular cartilage is strong and stiff (modulus between 1 and 20 MPa).

No wholly satisfactory procedure exists for replacing damaged articular cartilage in osteoarthrosis and instead in the case of the two most frequently injured joints, the hip and knee, artificial prostheses are most commonly used to replace the entire joint. While these increase mobility and reduce pain they suffer from progressive wear, mechanical failure, adverse tissue reactions and loosening at their interphase with the bone. Accordingly, there has been much work around the area of providing a suitable implantable repair material with improved performance over the currently available prostheses.

One such device is described in WO 2007/020449 A2, describing a cartilaginous tissue repair device with a biocompatible, bioresorbable three-dimensional silk or other fibre lay and a biocompatible, bioresorbable substantially porous silk-based or other hydrogel partially or substantially filling the interstices of the fibre lay.

International patent application number PCT/IB2009/051775 (published under WO2009/133532 A2) discloses a silk fibroin solution and method that can be used to make an improved fibroin material that has been found to be efficient as an implant for cartilage repair. The method for the preparation of the regenerated silk fibroin solution comprises the steps of: (a) treating the silk or silk with an ionic reagent comprising aqueous solutions of one or more of ammonium hydroxide, ammonium chloride, ammonium bromide, ammonium nitrate, potassium hydroxide, potassium chloride, potassium bromide or potassium nitrate; (b) subsequently drying the silk or silk cocoons after treatment of the silk or silk cocoons with the ionic reagent; and (c) subsequently dissolving the silk or silk cocoons in a chaotropic agent.

Furthermore, International patent application number PCT/GB2009/050727 (published under WO2009/156760 A2) discloses method for the preparation of an implantable material for the repair, augmentation or replacement of bone from a fibroin solution. The method comprises: preparing a gel from fibroin solution; preparing a material by subjecting the gel to one or more steps of freezing and thawing the gel, wherein the step of preparing the gel from the fibroin solution is performed in the presence of phosphate ions. The material is generally treated with calcium ions to form a fibroin-apatite. A further method step comprises the step of treating the material with an isocyanate to form cross-links. The implantable material has been found to be efficient as an implant for bone repair.

Whilst implantable cartilaginous tissue repair devices of the prior art are all useful in the repair, augmentation or replacement of damaged cartilage, many such devices suffer from a number of problems, such as: a) failure to anchor securely to existing bone or cartilage; b) failure to integrate with existing bone or cartilage; c) failure of the devices after implantation due to wrinkling, warping, shrinking, cracking or other structural deterioration or failure of the devices over time, or through loosening or complete separation of the device from its anchor; and d) failure of the device to maintain its overall shape under load within or on the repaired tissue.

It is an aim of embodiments of the present invention to provide an implantable repair device capable of load bearing and with improved or enhanced abilities to integrate with existing bone or cartilage. It is another aim of embodiments of the present invention to provide an implantable repair device adapted to provide improved articulation of the joint following cartilage replacement.

It would also be advantageous to provide an implantable tissue repair device with improved anchoring in bone or cartilage, and with improved resistance to anchoring means of the device being detached or torn from the device.

It would furthermore be advantageous to provide a device which is flexible under load but which is relatively resistant to permanent shape change, such as wrinkling, warping and shrinking, after implanting the device within or on damaged tissue.

It would also be advantageous to provide a device which overcomes or mitigates at least one problem of the prior art described herein.

SUMMARY OF THE INVENTION

According to a first aspect of the invention there is provided an implantable tissue repair device comprising:

a body comprising a biocompatible hydrogel; and a plurality of tissue anchoring elements projecting from the body;

wherein the anchoring elements are integrally formed with the body and comprise the same biocompatible hydrogel as the body, and wherein the anchoring elements, in use, are arranged to enter apertures in a tissue and anchor the device to the tissue.

The body of the device may comprise a front surface and a back surface, and the anchoring elements may all be located on the back surface. The front and back surfaces may be curved. The back surface of the device may be arranged, in use, to contact a tissue.

The anchoring elements may be substantially cylindrical in shape, and may have a circular or elliptical cross-section. In other embodiments, the anchoring elements may have a quadrilateral cross-section, such as square or rectangular, or may have another regular polygonal cross-section. In yet other embodiments, the anchoring elements may have a lobed cross-section. The anchoring elements may taper and may taper either outwardly or inwardly to the distal, free end thereof.

There may be at least 2, 3, 4, 5, 6 or 7 or more anchoring elements, preferably at least 3 and more preferably at least 5. In embodiments of at least 4 elements, the anchoring elements may form a substantially cruciform shape on the back surface of the body. In some embodiments there are at least 5 anchoring elements forming a cruciform shape on the back surface of the body, with at least one element forming each arm of the cruciform shape, and at least one element located centrally between the arms. In other embodiments at least some anchoring elements may form a ring or fringe, adjacent to, or located towards, the outer edge of the back surface of the body, and said embodiments may also further comprise one or more elements located within the ring or fringe, towards the centre of the back surface of the body. The afore-mentioned configurations of anchoring elements enable particularly effective anchoring of the devices of the invention to tissues in which corresponding apertures have been formed.

The body may comprise at least one fibre extending through at least a part of the device, such as a network of fibres. The network of fibres may comprise a two-dimensional network of fibres such as a layer, which may be in the form of a mesh, net or web layer. In some embodiments, the body comprises a three-dimensional network of fibres. Suitable three-dimensional networks include a plurality of stacked two dimensional networks (such as a plurality of layers), and matrices of fibres in three dimensions.

The fibre network may comprise wound or woven or knitted or embroidered or stitched or braided or knotted fibres, or compressed felts, or fabric layers.

The fibres in the fibre network may be formed from a biocompatible fibre material or a mixture of biocompatible fibre materials. Each fibre may comprise one or more natural materials, which may be selected from silk, cellulose or derivatives thereof, alginate, gelatin, fibrin, fibronectin, collagen, hyaluronic acid and chondroitin sulphate, or derivatives and/or mixtures thereof. Each fibre may comprise a synthetic material selected from polyethylene, nylon, ultra-high weight polyethylene, polylactic acid, polyglycolic acid, prolene or mixtures thereof, for example. Each fibre in the fibre network may be independently selected from any of the aforesaid materials. The fibre network may comprise at least one fibre formed of a natural material and at least one fibre formed of a synthetic material. Each fibre may be formed from a mixture of materials, such as a mixture of a natural material and a synthetic material, for example. In preferred embodiments, the fibres comprise silk, and may be mulberry, wild or spider silk fibres. The silk fibres may be obtained from the mulberry silkworm (*Bombyx mori*), wild silkworm, spiders or moth larvae from moth genera selected from *Antheraea, Cricula, Samia* and *Gonometa*, for example.

The fibres or the fibre network may be partially fused, melded or dissolved in the body of the device, such that an outer surface of the fibres substantially blends, melds or merges into the body of the device. This forms a stronger, reinforced body, increasing the strength of the device.

In embodiments where the body comprises at least one fibre network or layer, there may be threads stitched through the at least one fibre network or layer of the body to the outside of the body. The threads may be stitched to the outside of the back surface of the device, i.e. to the outside part of the body which comprises the back surface of the device, from which the anchoring elements protrude. In such embodiments, the threads may be woven between the anchoring elements to form a network.

At least one fibre, preferably at least one fibre layer, may be present in each anchoring element. In some embodiments, at least one fibre of the fibre network of the body extends into each anchoring element. In other embodiments, each anchoring element may comprise its own fibre or fibre network, which may be unattached or attached to the fibre network of the body.

In some embodiments, one or more fibres may project from one or more surfaces of the body and/or one or more fibres may project from one or more surfaces of each anchoring element.

In some embodiments the body of the device comprises at least one layer of fibres and each anchoring element may comprise at least one layer of fibres. A layer of fibres in each anchoring element may be located at or towards the free, distal end of the anchoring element. At least one layer of fibres in the body may be located at or towards the junction between the body and the anchoring elements projecting therefrom.

In embodiments in which the anchoring elements include at least one fibre layer at the free, distal end of the elements, the fibre layer may be exposed to the environment. In such embodiments the fibre layer, when contacting a tissue, in use, increases friction and grip.

In embodiments in which the anchoring elements comprise a layer of fibres (preferably at the distal, free end thereof), the elements may include at least one thread, stitched through the layer of fibres, and extending into the anchoring element. Each thread may extend from the fibre layer substantially perpendicular to the fibre layer (and thus substantially parallel with the longitudinal axis of the anchoring element). There may be at least one, preferably two or more, threads extending substantially parallel with the longitudinal axis of the anchoring element.

In embodiments in which the body comprises at least one fibre layer and the anchoring elements comprise at least one fibre layer, each thread may extend between at least one fibre layer in the body and at least one fibre layer in the anchoring element and may be stitched to each layer. There may be multiple stitches extending between the fibre layer in the body and the fibre layer in the anchoring element.

The threads may be formed from a biocompatible material such as polymeric suture material. Suitable thread materials include nylon, polyester, polypropylene, silk or polybutester. The threads may be monofilament threads or multifilament threads. The threads are preferably non bioabsorbable.

Stitching threads within the anchoring elements adds structural components within the anchoring elements to better transfer forces to the fibre layer or layers of both the body and anchoring elements; and increases stiffness and strength of the anchoring elements.

The hydrogel may comprise at least one material selected from silk fibroin, gelatin, fibrin, fibronectin, alginate, collagen, hyaluronic acid and chondroitin sulphate, or derivatives thereof. In preferred embodiments the hydrogel comprises silk fibroin. The silk fibroin may be derived from spider silk, silk created by the larvae of mulberry silkworms (*Bombyx mori*), wild silkworms or larvae of moths from the genera *Antheraea, Cricula, Samia* or *Gonometa*, for example. The silk fibroin may be regenerated silk fibroin and may be selected from regenerated mulberry, wild or spider silk fibroin.

In some embodiments the hydrogel comprises silks fibroin and the or each fibre layer or network comprises silk fibres.

Preferably, at least a part of the body is porous. In some embodiments, the whole body is substantially porous. In preferred embodiments, the body and the anchoring elements are porous. The pores of the body and anchoring elements may independently range from approximately 10 µm to approximately 1000 µm in average diameter. The average pore diameter may range from approximately 100 µm to approximately 500 µm, more particularly, approximately 200 µm to approximately 400 µm. The average pore size may be approximately 300 µm.

The porous part of the body and/or the porous anchoring elements may comprise at least 10%, at least 20%, at least 25%, at least 30%, at least 40%, at least 50%, at least 60%, at least 70%, at least 80%, or at least 90% porosity by volume, such as between approximately 10% and approximately 95% porosity by volume. Preferably, the body and/or anchoring elements comprise between approximately 60% and approximately 95% porosity by volume. More preferably, the body and/or anchoring elements comprise between approximately 65% and approximately 95% porosity by volume. Most preferably, the body and/or anchoring elements comprise approximately 65-80% porosity by volume.

Preferably, the porous part of the body and/or anchoring elements comprise an open porous network, with a substantial proportion of "open pores", with at least some pores communicating with adjacent pores, and each pore may form a branched structure of channels, as opposed to "closed pores" which form separate discrete voids.

The open pores may form less than 50% of all pores, but preferably form at least 55%, 60%, 65% or at least 70% of all pores by volume, preferably, approximately more than 80% of all pores by volume, more preferably, approximately more than 95% of all pores by volume and most preferably, approximately more than 99% of all pores by volume.

In some embodiments, the body comprises at least one porous surface. The porous surface may comprise the back surface of the body of the device. More preferably, therefore, the porous layer is a continuation of the porous portion of the body. The porous surface may communicate with the pores of the body, and the majority of the pores on the surface of the body may communicate with pores within the body, via the open porous network. At least part of the outer surface of each anchoring element may comprise a porous surface, and the pores of the said surface may communicate with pores located within the anchoring elements. Therefore, in some embodiments the body comprises a porous surface on the back surface of the body and the anchoring elements also comprise a porous surface.

The or each porous surface may be mineralised. The body and/or anchoring elements may be selectively mineralised. By "selectively mineralised" we mean selected areas of the body and/or anchoring elements are mineralised. Most preferably, the body, including the porous surface, and the anchoring elements, including the porous surface thereof, are mineralised.

Preferably, the selected areas of the body and anchoring elements are mineralised with calcium phosphate, most preferably, with hydroxyapatite. Preferably, the hydroxyapatite is present as a nanocomposite throughout the selected porous areas of the body.

Alternatively, calcium phosphate crystals may be nucleated onto the porous surface(s). Alternatively, still, calcium phosphate crystals may be nucleated onto the porous surface(s) and throughout the selected areas of the body and/or anchoring elements.

Alternatively, the selected areas of the body and/or anchoring elements are mineralised with granules of hydroxyapatite or calcium phosphate. The granules may be attached using an adhesive or cast into the body and/or anchoring elements and/or may be secured onto any fibres present in any fibre networks.

The granules may be approximately 0.2 mm to approximately 2 mm in diameter. Preferably, the granules are approximately 0.3 mm to approximately 1.5 mm in diameter. The granules may be between approximately 0.3 mm and approximately 0.7 mm in diameter, or between approximately 0.7 mm and 1.5 mm in diameter. Additionally or alternatively, some or all of the granules may be provided as small as 140 µm in diameter.

The device may have a thickness of approximately 0.2 mm to approximately 25 mm thick. The body of the device may have a thickness of between 0.1 mm and 20 mm, such as between 0.1 mm and 15 mm, or preferably between 0.1 mm and 12.5 mm, and the anchoring elements may project a further 0.1 mm to 15 mm, or between 0.2 mm and 10 mm. In some embodiments the body comprises a thickness of between 7.5 mm and 12.5 mm and the anchoring elements project a further 0.25 mm to 10 mm, especially a further 3 mm to 8 mm, and most preferably around 4 to 7 mm. The anchoring elements may have a length of approximately 75%, 65%, 50%, 33% or 25% of the thickness of the body.

The device may have a total thickness of between 0.2 mm and 6 mm. Such "thin" devices may be particularly suitable for resurfacing damaged tissue, in use. Alternatively, the device may have a total thickness of between 6 mm and 20 mm, preferably between 6 mm and 15 mm, and more preferably between 6 mm and 12 mm. Such "thick" devices may be particularly suitable for tissue replacement or augmentation, including replacement of subchondral bone, in use.

The device or body of the device may be shaped to mimic the shape and contours of the tissue component that it is intended to replace or repair. For example the shape of the device or body of the device may conform to the edges of a hole or cavity formed in a tissue, in order to fill said hole or cavity. In another embodiment, the device may be disc shape, for use in re-surfacing of a tissue. In yet other embodiments the device may have a regular polygonal or polyhedral shape, such as cuboid; may be hemispherical; may be lobed; or may have an irregular shape such as a figure of eight shape, kidney shape, heart shape or bow tie shape, for example. Alternatively, or additionally, the device may be flexible, such that it may adapt to the contours of the tissue on which, or in which, it will be located.

The hydrogel in the body and/or anchoring elements may be cross-linked. In embodiments where the hydrogel comprises a proteinaceous material, such as silk fibroin, it can be cross-linked using one or more covalent cross-linking agents. In embodiments where the hydrogel comprises fibroin, the hydrogel can be cross-linked by hydrogen bonds by treatment with, for example, 30-70% v/v ethanol. Either form of cross-linking influences the mechanical properties of the hydrogel. A range of different cross-linking agents may be used, and the cross-linking agent may be selected from an aliphatic aldehyde, dialdehyde, carbodiimide, succinimide, succinamide, peroxidase in the presence of hydrogen peroxide, transglutaminase, phenoloxidase, tyrosinase, isocyanates and Fenton reaction catalyst.

The body and anchoring elements may be relatively stiff but flexible, and may be resilient.

In embodiments in which the hydrogel of the body and/or anchoring elements includes one or more fibres, the hydrogel may be further cross-linked to the fibre(s). Cross-linking of the hydrogel to the or each fibre or fibre network may be via any of the aforesaid cross-linking agents or processes.

In some embodiments, the hydrogel of the anchoring elements comprises both threads and cross-linking, as described above; and in yet other embodiments the hydrogel in the body of the device comprises cross-linking and the hydrogel in the anchoring elements comprises both threads and cross-linking. In preferred embodiments the body and anchoring elements comprises one or more fibres or fibre layers as described hereinabove, the hydrogel in the anchoring elements comprises threads and cross-linking, and the hydrogel in the body comprises cross-linking. In such embodiments the combination of fibre network, cross-linked hydrogel and supporting threads provides excellent stiffness to the device.

In some embodiments, the device is a meniscal repair device, suitable for repairing or replacing the menisci of a joint, particularly a knee meniscus. In other embodiments the device is an intervertebral disc repair device, suitable for replacing or repairing intervertebral discs. In further, preferred embodiments, the device is an articular cartilage repair device, suitable for repairing or replacing articular cartilage. Preferred embodiments comprise a meniscal repair device, articular cartilage repair device or an intervertebral disc repair device comprising a porous silk fibroin hydrogel in both the body and anchoring elements, wherein the body and anchoring elements both comprise at least one silk fibre network layer.

The present invention provides an implantable tissue repair device with mechanical properties which are closer to the anatomical requirements of the tissue to be repaired than those of prior art devices. Indeed, an appropriately constructed device according to the present invention is capable of carrying out the mechanical functions of replaced tissue from the moment of implantation.

The present invention also provides an implantable tissue repair device which allows and encourages the gradual infiltration and in some embodiments replacement of at least some parts of the device with autologous collagen and proteoglycans (i.e. collagen and proteoglycans produced by the patient's own body) more effectively than prior art devices. The porosity of the hydrogel allows, in particular, for infiltration by mesenchyme or stem cells.

The present invention provides a device which enables the mechanical properties of the prosthesis to be tuned locally to provide appropriate stress/strain environments throughout the prosthesis to avoid the problem of stress shielding thereby encouraging the de novo formation of the correct connective tissues appropriate to the different locations of a complex tissue.

In embodiments comprising a network of fibres, the two- or three-dimensional fibre network and constrained hydrogel impart cartilage-like properties to the implantable device enabling it to distribute stresses during compressive loading and, in the case of menisci and intervertebral discs, to act as a shock absorber. In fibre network-containing embodiments, the orientation of collagen fibres in the natural tissues can be closely mimicked by the fibres of the implantable device of the present invention, giving it anisotropic mechanical properties similar to those of the natural tissue.

The devices of the invention include an integral means of attaching or anchoring the implantable device firmly to the bone (or other tissue) of a patient, in the form of the integrally formed anchoring elements, which helps to overcome a persistent weakness of many orthopaedic devices— mechanical failure at the bone/prosthesis interface.

In some embodiments of the invention, comprising a silk fibre network in the body and/or anchoring elements, a fibre network of strong, elastic and tough silk fibres entraps and/or is bonded to a porous hydrogel matrix cross-linked and/or bonded to the silk fibres, which gives a tough, resilient composite material with a high modulus.

According to a second aspect of the invention there is provided an implantable tissue repair device comprising:

a body comprising a biocompatible hydrogel; and a rigid support at least partly located within the body or device, or connected to the body or device.

The support may comprise a rigid polymeric material, a ceramic material, a metal, an alloy, or any combination thereof.

Suitable metals include titanium, Tritanium® and tantalum for example. Suitable alloys include stainless steel, cobalt alloys, titanium alloys, tantalum alloys, for example.

Suitable polymeric materials include polyethylene, polyamide, polytetra fluoroethylene, polyetheretherketone (PEEK) and polyurethane, for example.

Suitable ceramic materials include aluminium oxide, zirconium oxide, hydroxyapatite, tricalcium phosphate, bioglass and carbon-silicon materials, for example.

The support may be entirely surrounded by the hydrogel, or one or more part, side, vertex or edge of the support may be exposed from or protrude from the hydrogel and/or body. The support may be embedded in the hydrogel body, or the hydrogel body may at least partially infiltrate at least part of the support The support may comprise one or more apertures, cavities or channels therethrough, and may be porous. In embodiments with a porous support, then pores may form an open porous network. The hydrogel may at least partially penetrate into the pores of the support.

The support may comprise a plate, which may have one or more apertures, cavities, pores or channels therethrough. The plate may comprise an array of apertures, cavities, pores or channels which run through the plate from top to bottom. The plate may have a thickness of between 5% and 80% of the thickness of the hydrogel body, such as between 10% and 50% or between 20% and 40%, for example. The plate may be entirely located within the body such that it does not protrude therefore, or may project from one or more surfaces of the body.

Alternatively, the support may comprise a rigid framework. In its simplest form the rigid framework may comprise a single frame member. The frame member may be in in the form of an elongate strut or rib, or a plate, for example, and may include one or more apertures, cavities or channels therethrough; but in preferred embodiments the framework comprises two or more frame members.

The rigid framework may comprise a plurality of frame members connected to form the framework. The framework may comprise a plurality of integrally formed frame members.

The rigid framework may be a rigid net, mesh or layer, which may be substantially two-dimensional. There may be two or more such frameworks such as two or more layers. Alternatively, the framework may comprise a three-dimensional framework, such as a 3D lattice.

The framework may comprise a hollow framework, which may comprise a plurality of frame members surrounding a cavity. In some embodiments the framework may comprise two or more cavities, each cavity surrounded by frame members.

The framework may comprise a 3D lattice structure comprising two or more hollow cells. The cells may be cubic, tetragonal, orthorhombic, rhombohedral, hexagonal, monoclinic, triclinic, or a combination thereof. In some embodiments, the cells may be irregular in shape.

The rigid support may be indirectly connected to the body. The rigid support may comprise a plurality of support members connected to the body of the device by an intermediate connection, which in some embodiments may be a wire, thread or the like, for example. In embodiments where the rigid support is indirectly connected to the body by an intermediate connection, the rigid support may comprise a plurality of ribs, struts, plugs or elongate members, each connected to a separate intermediate connection. The plurality of support members may be spaced apart from the body by the intermediate connection or connections.

The body may further comprise a network of fibres. The network of fibres may be as described hereinabove for the first aspect of the invention, and may be relatively flexible. In some embodiments the body comprises at least one layer of fibres located substantially within the body. The rigid support may be connected to the network or layer of fibres. The network or layer of fibres may be located above the rigid support, and in some embodiments, may rest on the rigid support, whilst in other embodiments the or each layer of fibres may be separated from the rigid support by the hydrogel.

The device of the second aspect of the invention may further comprise at least one anchoring element projecting from the body. The anchoring elements may comprise parts of the support projecting from the body of the device and therefore may comprise rigid anchoring elements. The rigid support may comprise a rigid framework and the anchoring elements may comprise at least one frame member projecting from the body, and preferably projecting from a back or bottom surface thereof.

The rigid anchoring elements may be porous and/or comprise a porous outer surface. Porous anchoring elements are particularly useful for enabling infiltration of biological material when used.

The rigid anchoring elements may comprise a band of solid, substantially non-porous material (such as titanium, for example), which separates at least a portion of the porous rigid anchoring elements. The band of solid material may separate a distal portion of the porous rigid anchoring elements. Thus, the band of solid material may be arranged to prevent hydrogel from the body seeping into said porous distal end, during manufacture or use. This may allow the pores of the separated distal end of the rigid anchoring elements to remain clean/unfilled (especially if combined with a coating layer around the anchoring elements, such as a sacrificial wax layer), thereby allowing more efficient infiltration of biological material after implantation.

The rigid anchoring elements may be hollow. The cavity formed within the hollow anchoring elements may be at least partially filled with the same biocompatible hydrogel material of the body of the device and the hydrogel in the anchoring elements and body may be integrally formed. The hollow anchoring elements may include one or more apertures in communication with the interior and exterior of the elements, and any hydrogel or material within the elements.

The cavity within the hollow anchoring elements may be exposed at the free, distal end of the elements (and therefore be in communication with the outside environment). In such embodiments any hydrogel within the cavity will also be exposed to the outside environment, and therefore in use, when the anchoring elements are inserted into cavities within a tissue, biological material and fluid may infiltrate the hydrogel within the anchoring elements.

The rigid anchoring elements may further be at least partially coated, and may be fully coated, with the biocompatible hydrogel, which hydrogel may be integrally formed with the hydrogel of the body. Alternatively, the rigid anchoring elements may be coated with a masking material which prevents any hydrogel or other material from contacting or coating the surface of the anchoring elements. The masking material may be removed before use of the device. The masking material may comprise wax, a polymeric material or the like, for example.

In other embodiments, anchoring elements may be integrally formed with the body, and wherein the anchoring elements comprise the same biocompatible hydrogel material as the body. The anchoring elements may be as described and defined hereinabove for the first aspect of the invention and may not include any rigid support within the anchoring elements.

Any integrally formed hydrogel anchoring elements may comprise at least one rigid support, rigid frame member or a rigid framework, which may be as described hereinabove in relation to the rigid support, frame member and rigid framework of the body and/or rigid anchoring elements. In preferred embodiments at least one frame member of the rigid framework of the body extends into the anchoring elements. The framework in the body and the frame member or framework in the anchoring elements may comprise the same integrally formed framework. In other embodiments, the framework of the body and the frame member or framework in the anchoring elements are unconnected. In some embodiments the device comprises a rigid support in each anchoring element only, while in other embodiments the device comprises a rigid support in each anchoring element and in the body, and the rigid supports in the anchoring elements may or may not be connected to the rigid support in the body. Any rigid support in the anchoring elements may be connected to a fibre network or layer in the body.

The anchoring elements may comprise a network of fibres, as described hereinabove for the device of the first aspect of the invention. The network of fibres may comprise at least one fibre layer, and in preferred embodiments comprises at least one fibre layer located at or adjacent to the free, distal end of the anchoring element. The fibre layer may be exposed or protrude from the free, distal end. The fibre network in the anchoring elements may be connected to a fibre network in the body, such as by stitching with a thread, wire or the like, for example.

In some embodiments, the device comprises at least one fibre layer located on top of the rigid support of the body, and at least one fibre layer located at, or adjacent to, the free distal end of the anchoring elements.

In some embodiments the anchoring elements and/or body comprise at least one thread, as described above for the first aspect of the invention. In some embodiments, the thread or threads are stitched to or around the rigid support of the body and/or anchoring elements. Therefore in some embodiments the anchoring elements and body may comprise separated rigid supports which are connected via threads. In embodiments where one or more external rigid supports is connected to the body via an intermediate connection, the body may comprise a rigid support which is connected to the external rigid support via the intermediate connection. In some embodiments, the threads are woven together and form a woven network of threads. The woven network of threads may run through channels, pores, apertures and/or cavities in the rigid support, and/or around a side (laterally and/or vertically) and/or along a surface of the rigid support. The woven network of threads may run around one or more side (laterally and/or vertically) of the hydrogel body and/or a fibre layer in the body. In such embodiments, a fibre layer may be located above the rigid support, and said woven network of threads may be stitched to said fibre layer. This may secure the rigid support within or to the hydrogel body, especially in embodiments where the rigid support is embedded in or secured to the hydrogel body. In such embodiments, there may be a fibre layer located below the rigid support alternative or additional to the woven thread network beneath the rigid support. The fibre layer below the rigid support may be stitched to the fibre layer above the rigid support by threads. In embodiments with anchoring elements, there may be a fibre layer extending around the anchoring elements, preferably at the upper end thereof, abutting or adjacent to the support body from which the anchoring elements protrude.

In some embodiments the device comprises at least one fibre layer located on top of a rigid support of the body, and at least one fibre layer located below a rigid support in the anchoring elements, and the fibre layers are connected with threads, wires or the like; and thus in such embodiments the rigid supports of the body and anchoring elements are bound between said fibre layers.

The use of a rigid framework within the body and anchoring elements (or forming the anchoring elements) provides structured support to ensure the device as a whole, and in particular, the hydrogel, maintains its shape for extended periods of time, during use. In addition the rigid framework prevents or mitigates wrinkling or flexing of the hydrogel under varying environments (such as low humidity or low water environments) and ensures that the shape and contours of the device are maintained throughout storage, implantation and subsequent use.

In addition, the combination of a rigid support or framework within the body or connected to the hydrogel, and rigid anchoring elements, which rigid support or framework is connected to a fibre layer above and/or below the support or framework ensures that movement of the framework or support within the hydrogel, or detachment of the hydrogel from the rigid support or framework is prevented or mitigated thereby preventing or mitigating tearing or distortion of the hydrogel and device from within. The use of threads (or other ties) stitched between the fibre network(s) and framework further serves to stabilise and strengthen the device and prevent the framework and fibre network from moving.

The body, hydrogel, fibres, anchoring elements, threads and cross-linking agents described in relation to the devices of the first aspect of the invention may be used in the second aspect of the invention and thus the body, fibres, anchoring elements, threads and cross-linking agents may be as defined and described hereinabove for the first aspect of the invention.

The rigid framework may comprise a porous rigid framework, and any frame members may be porous.

According to a third aspect of the invention therefore, there is provided a method of preparing an implantable tissue repair device of the first aspect of the invention or a portion or layer of such a device, the method comprising the steps of: preparing a hydrogel material in a mould corresponding to the shape of the device or portion or layer thereof; and optionally subjecting the hydrogel to one or more steps of freezing and thawing the hydrogel.

According to a fourth aspect of the invention therefore, there is provided a method of preparing an implantable tissue repair device of the second aspect of the invention or a portion or layer of such a device, the method comprising the steps of: preparing a hydrogel precursor material in a mould; at least partially inserting a rigid support into the precursor material or laying a rigid support on the precursor material; gelling the hydrogel precursor material to form a hydrogel; and optionally subjecting the hydrogel to one or more steps of freezing and thawing the hydrogel.

The rigid support may be as described hereinabove for the second aspect of the invention.

The following statements apply to the methods of both the third and fourth aspects of the invention.

The use of one or more freeze-thaw cycles ensures the hydrogel contains pores, and particularly an open porous network.

By "mould" we mean a vessel in which subsequent hydrogel is contained.

The method may comprise a step of forming a porous surface on the hydrogel, after the freezing and thawing step(s).

Preferably, creating a porous surface on said device comprises the step of removing at least a portion of a surface of the device to expose the pores thereunder. Preferably, therefore, substantially all of the mould is adapted to provide smooth surfaces on the hydrogel.

Preferably, removal of the surface includes cutting away the said surface from the hydrogel. Any suitable method may be used to expose the porous surface, such as shaving, abrading, or dissolving away said surface.

Alternatively, the mould may be adapted to provide the porous surface. In this case, approximately 50% of the mould may be adapted to provide a smooth surface(s) on the hydrogel and approximately 50% of the mould may be adapted to provide porous surface(s) on the hydrogel. Alternatively, approximately 60% of the mould may be adapted to provide a smooth surface and in other applications approximately 20% of the mould may be adapted to provide a smooth surface. The mould may be adapted to provide a porous surface on the back surface of the device. In methods in which the device includes anchoring elements portions of the mould corresponding to the anchoring elements may be adapted to provide a porous surface.

A part of the mould may be polished.

The step of forming a hydrogel in the mould may comprise adding a solution of hydrogel precursor material to the mould and gelling said solution. The hydrogel precursor material or solution may comprise a solution of monomers, dimers, oligomers or polymeric material. The solution may comprise a solution of silk fibroin, in preferred embodiments.

The method may comprise incorporating a fibre network, such as biocompatible fibres or at least one fibre layer, in the device. The method may therefore comprise providing a fibre network, such as a fibre layer (which may be formed by winding or weaving or twisting or knitting or braiding or stitching or embroidering fibres, or compressing felts or combining layers of cloth). The fibre layer may be formed so as to be substantially biomimetic of the fibre pattern of a tissue to be repaired.

The method may comprise at least partially infiltrating the fibres or fibre layer with the hydrogel. Therefore, the method may comprise the additional step of positioning the fibres or fibre layer in the mould with the hydrogel precursor material or solution.

Preferably, the method comprises adding the fibres or fibre layer to the solution prior to gelling of the hydrogel. Preferably, the fibres or fibre layer are/is partially dissolved in the hydrogel precursor before gelling the precursor around the fibres/fibre layer. This allows outer layers of the fibres to substantially blend or merge with the hydrogel matrix therearound, in the final body of the device.

Preferably, any fibres or fibre layer comprises silk fibroin.

Preferably the device comprises a body and anchoring elements, as described hereinabove.

The method may comprise providing at least one mould part for forming the body of the device and at least one mould part corresponding to the shape of the anchoring elements. The method may comprise locating at least one fibre layer in, or adjacent to the mould part forming the body of the device. The method may comprise locating at least one fibre layer in the mould part forming the body of the device at or towards a location in the mould corresponding to the upper surface, lower surface or both the upper and lower surfaces of the body of the device. Preferably the method comprises locating a fibre layer at the junction of the mould parts forming the body of the device and the anchoring elements. The method may comprise the step of locating at least one fibre layer in, or adjacent to, the mould part corresponding to the anchoring elements. In preferred embodiments a fibre layer is located on or in the mould part corresponding to the free, distal ends of the anchoring elements.

Preferably, at least a part of the mould comprises a dialysis membrane, dialysis bag, dialysis vessel or dialysis surface and the solution is gelled against the dialysis membrane, bag, vessel or surface in order to achieve a skin with the smooth surface. The method may use a dialysis membrane, bag, vessel or surface comprising a cellulose acetate dialysis membrane.

Alternatively, the solution may be gelled against a glass surface or other smooth surface.

Alternatively, the method may comprise subjecting the device to post-forming processing in order to achieve a smooth surface.

Preferably, the solution is gelled by treating the solution with an aqueous solution of one or more gelling reagents or activators, such as, for example, an acid. By way of example, particularly good results have been achieved using a gelling agent comprising an acetic acid solution. Gelation may be performed at a temperature of approximately 20° C. using a 1% solution of acetic acid for a period of time determined by the depth of penetration of the gelation required. For example, with a device approximately 8 mm thick, gelation time may be between approximately two and eight hours, more preferably, four to six hours.

Any mould may be removed prior to freezing and thawing steps. Preferably, the freezing (but not necessary the thawing steps) are conducted with any mould in place.

Freezing of the hydrogel may be performed at any suitable temperature, for example, within a temperature range of approximately −1° C. to approximately −120° C. Preferably, freezing is performed within a temperature range of approximately −10° C. to approximately −30° C. More preferably, freezing is performed within a temperature range of approximately −14° C. to approximately −20° C. For example, good results have been achieved where freezing is performed at a temperature of approximately −14° C. to −18° C.

A plurality of freezing and thawing cycles may be performed to increase the diameters of the pores.

The method may comprise forming the body and anchoring elements of the device from a regenerated fibroin solution, such as that disclosed in WO2009/133532 A2, the contents of which are incorporated herein by reference.

When using a regenerated fibroin solution, silk or silk cocoons may be degummed (removing the sericin) either before or after or consecutively with the treatment with an ionic reagent. Degumming may use a proteolytic enzyme that selectively cleaves sericin, but not fibroin, such as trypsin. The subsequent dissolving of silk in a chaotropic agent may be a chaotropic agent of up to 9.4M and/or for a period of time of less than 24 hours, more preferably using an agent of between approximately 8.0M and 9.4M, even more preferably, at 37° C. Most preferably, dissolving of silk in a chaotropic agent may comprise a solution of approximately 8.25M to 9.0M, again, preferably at 37° C. Good results have been achieved at 37° C., 8.5M of chaotropic agent concentration and less than 12 hours of time. Preferably, the chaotropic agent is lithium bromide.

Preferably, the method comprises steps in the following order: (a) providing a hydrogel precursor solution; (b) freezing the solution in a mould; (c) removal of the mould; (d) simultaneous thawing and gelling of the solution; and (e) subjecting the hydrogel to one or more freeze/thaw cycles. Step (a) may comprise dialysis of the hydrogel precursor solution.

Prior to step (a), preferably, individual fibres or a fibre layer are/is introduced to the hydrogel precursor solution (optionally with a chaotropic agent, for example if the gelling material is silk fibroin or regenerated silk fibroin). This has the effect of introducing a controlled/partial dissolution of the introduced fibres/fibre layer, (such as by commencing removal of the chaotropic agent during dialysis).

When a chaotropic agent is used, dialysis against pure water, polyethylene glycol solution or another suitable solvent may be used to remove any chaotropic agent, and the solution may be concentrated to approximately 5-25% w/v.

In step (b), the freezing helps to retain the shape of the solution in the shape of the mould, prior to step (c).

Preferably, step (d) comprises gelling using any suitable gelling agent, such as an acid. By thawing during gelling, the shape of the mould is retained.

Step (e) introduces pores into the hydrogel.

The method may comprise stitching at least one thread between two fibres in the fibre network. The method may comprise stitching at least one thread between two fibre layers, and may comprise stitching at least one thread between a first fibre layer located in or adjacent to the anchoring elements and a second fibre layer located in the body of the device. Stitching each thread may be undertaken before or after formation of the hydrogel, preferably before, and thus stitching is preferably performed before step (a) and the stitched or sutured fibres or fibre networks located in a mould before addition of the hydrogel precursor solution.

The method may comprise removing the gelled hydrogel from the device and trimming or cutting the hydrogel into the final shape of the device. Trimming or cutting may comprise removing excess material from around the periphery of the device.

The mould may include one or more apertures or openings which in use enables infiltration of the solution into the mould.

According to a fifth aspect of the invention there is provided an apparatus for manufacturing a device of the first or second aspects of the invention comprising a mould and an anchoring element forming device, the mould comprising a mould part for forming the body of the device, wherein the mould part and anchoring element forming device are operably connected to enable integral formation of the body and anchoring elements.

The device for forming the anchoring elements may comprise a mould for forming the anchoring elements, or may comprise a device for forming parts which are subsequently formed into the anchoring elements (such as by cutting, trimming or the like, for example).

The mould may comprise a single, integral mould, or may comprise multiple separate mould parts, which may be connected, or otherwise contact each other during moulding of the device. In preferred embodiments, there is a mould part corresponding to the front or upper side of the body of the device and single mould part corresponding to the anchoring elements and the back or lower side of the device. In use, the parts are connected, directly or indirectly to form an overall mould corresponding to the shape of the device.

The apparatus may comprise a frame arranged in use to secure the anchoring element forming device and, may also secure any fibre network of the device to be formed. The frame may comprise upper and lower frame members. The upper frame member may comprise or be connected to the upper mould part corresponding to the shape of the front or upper side of the body of the device, and the lower frame member may comprise or be connected to the lower mould part corresponding to the shape of the back or lower side of the body of the device.

The apparatus may comprise a device perimeter shaping part, which is arranged, in use to shape or enable shaping of the outer perimeter of the device during formation of the device in the apparatus. The device perimeter shaping part may comprise a central mould part, which may be located or clamped (such as in a sandwich configuration, for example) between the upper and lower frame members. The upper and lower frame members may be clamped together by any suitable means, such as by locking screws, clips or the like, for example.

The central mould part may comprise an aperture therethrough, the aperture defining the outer perimeter of the device to be moulded. The central mould part may comprise a sheet having an aperture therethrough. The upper surface of the central mould part or sheet may be contoured to form a contoured back or lower side of the body of the device; and may be convex to form a concave back of the body, for example.

The upper mould part may comprise a concave surface which in use forms a convex front or upper side of the body of the device.

The apparatus may further comprise a lower mould part. The lower mould part, when present, may be used to urge the anchoring element forming device into a desired shape and/or position, and may change the shape of the anchoring element forming device to adopt the corresponding shape of the back or lower side of the body of the device. The lower mould part may comprise a convex surface which in use will shape the anchoring element forming device into a configuration which includes a concave back or lower side of the body of the device. The lower mould part, in use may protrude or project at least partially through the aperture in the central mould part.

In use, one or more fibre layers may be clamped between the upper and lower frames and may be placed above or below the central mould part, in use, such that the fibre layers extend over and/or under the aperture of the central mould part. In some embodiments the fibre layers are clamped between the upper and lower frame members in the same manner as the central mould part.

In preferred embodiments at least a part of the fibre layer or layers are urged into a shape conforming to the final 3-dimensional shape of the body of the device. In preferred embodiments a fibre layer is located under the sheet or central mould part and a portion of the fibre layer is urged through the aperture of the sheet or central mould part to correspond substantially to the shape of the body of the device, in use. Urging of the fibre layer may be effected by the anchoring elements forming device and/or lower mould part, in use, as the anchoring elements forming device and/or lower mould part moves to project through the aperture in the sheet.

The device for forming the anchoring elements and/or the lower mould part may be arranged to urge any fibre layer (whether located under the sheet or over the sheet) into the shape of the body of the device.

The mould portion corresponding to the anchoring elements may be arranged below the central mould part. The mould portion corresponding to the anchoring elements may be urged at least partially through the aperture in the central mould part by the lower mould part as the lower mould part moves to project through the aperture, and may be arranged to urge any fibre layer (whether located under the sheet or over the sheet) into the shape of the body of the device, in use. In preferred embodiments the mould portion corresponding to the anchoring elements is urged substantially through the aperture of the central mould part, in use.

In alternative embodiments, the device for forming the anchoring elements is shaped to form both the anchoring elements and the lower or back side of the body of the device. In such embodiments the lower mould part, when present in the apparatus, may simply move the anchoring elements forming device into position in the apparatus, without changing its shape.

The mould portion corresponding to the anchoring elements may comprise a plurality of tubes corresponding to the shape of the anchoring elements. The tubes may be interconnected, such as by connection struts, for example. The mould portion corresponding to the anchoring elements may be clamped between the upper and lower frame members, and may be clamped below the central mould part (e.g. the sheet), when present.

In preferred embodiments the apparatus comprises in order from top to bottom, an upper frame member, an upper mould part corresponding to the shape of the front surface of the device, a central mould part in the form of a sheet having an aperture having dimensions corresponding to the perimeter of the device, a mould part corresponding to the anchoring elements and the back surface of the device, and a lower frame member.

The mould of the fifth aspect of the invention may be used in the method of the third or fourth aspect of the invention.

DETAILED DESCRIPTION OF THE INVENTION

In order that the various aspects of the invention may be more clearly understood, embodiments thereof will now be described, by way of example, with reference to the accompanying drawings, of which:

FIGS. 1 to 3 illustrate an embodiment of an implantable tissue repair device 2 of the first aspect of the invention.

Figure 1:
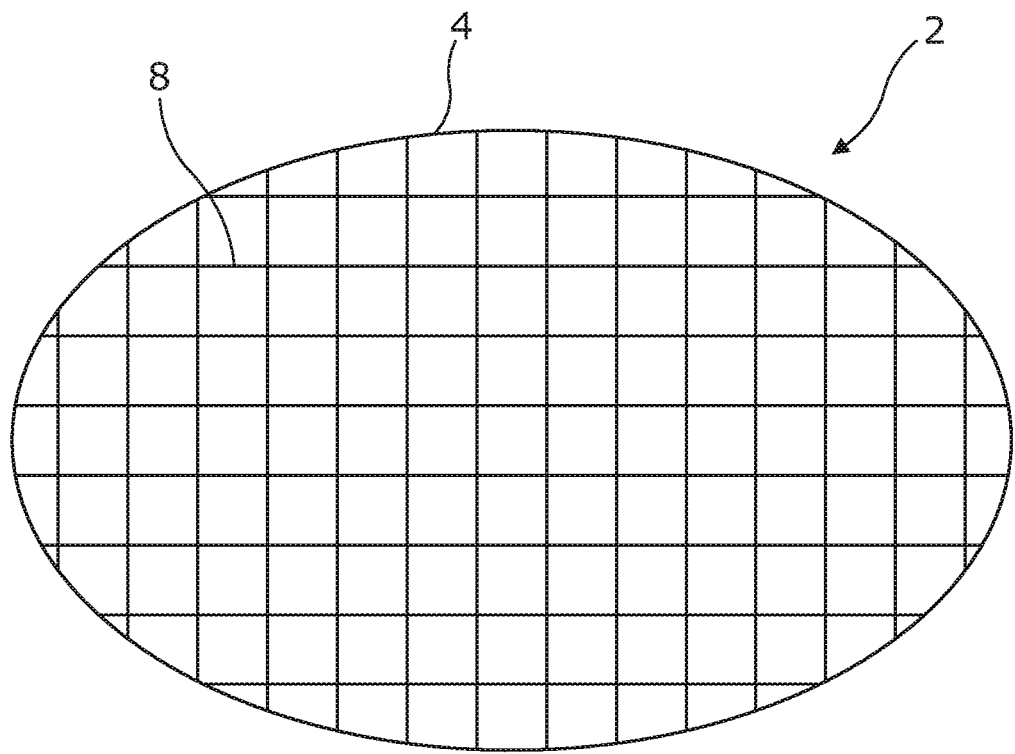
FIG. 1 illustrates a top-down view of an implantable tissue repair device of the first aspect of the invention.
Figure 2:
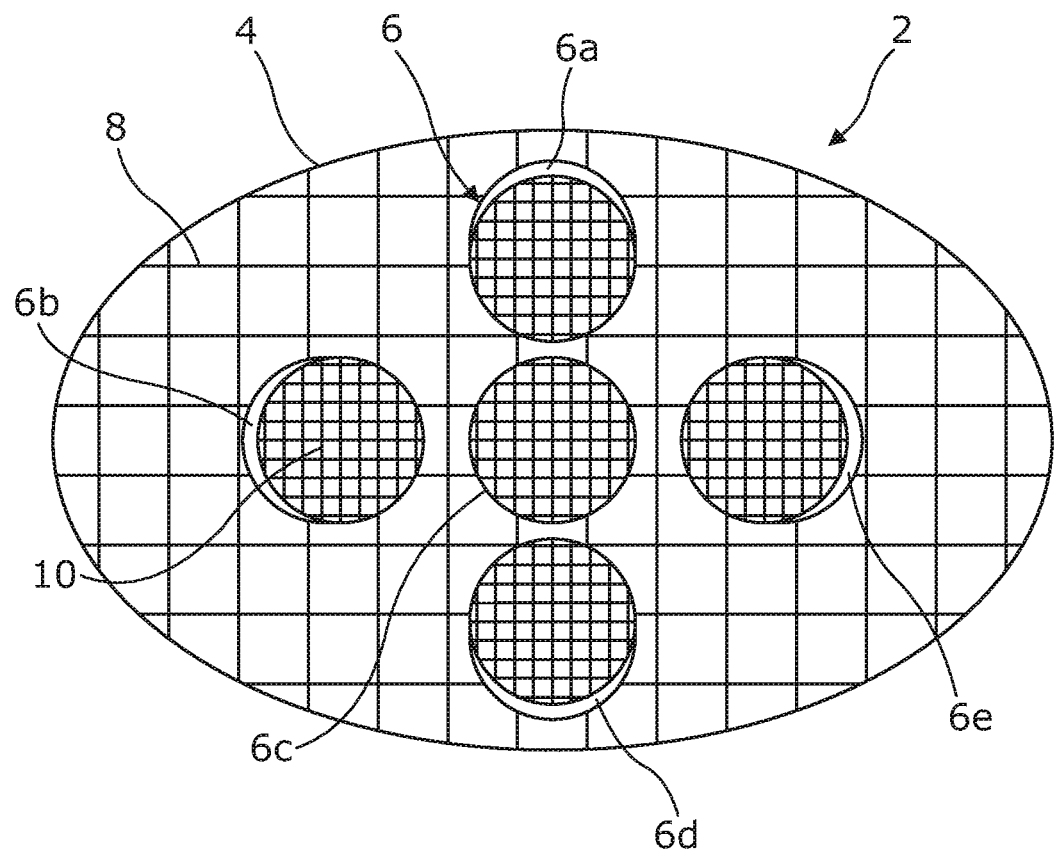
FIG. 2 illustrates a bottom-up view of the embodiment of FIG. 1.
Figure 3:
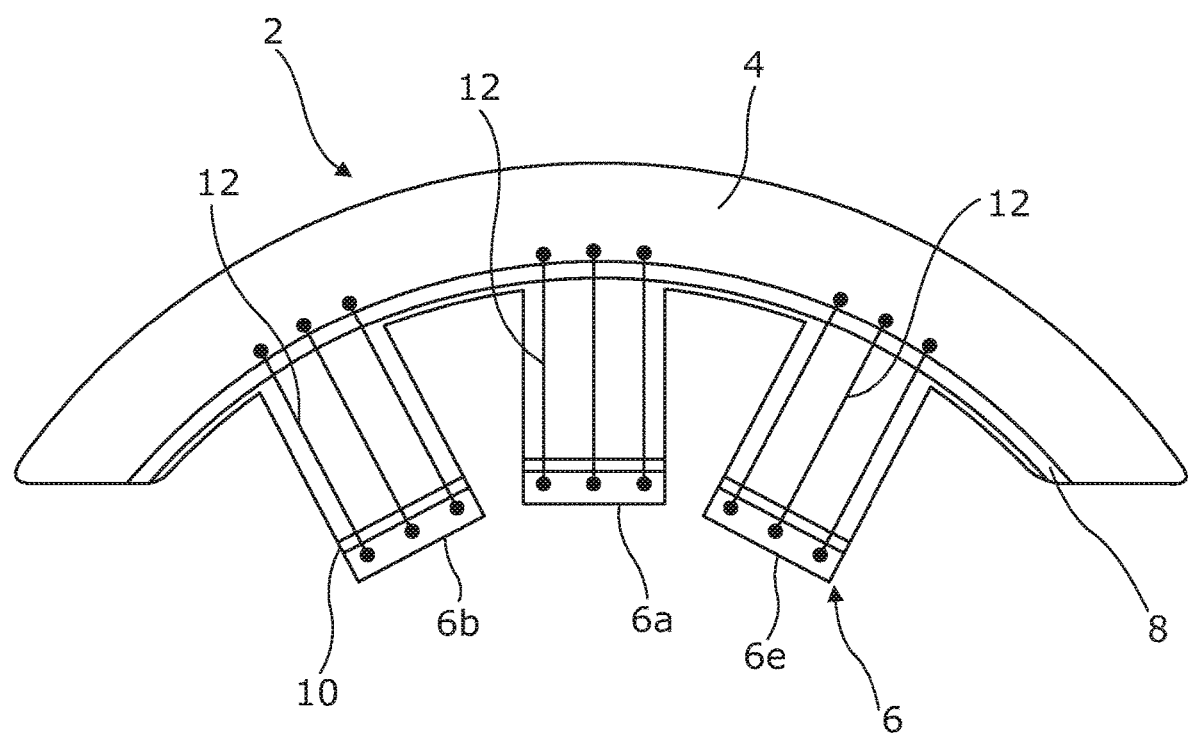
FIG. 3 illustrates a cross-sectional view from the side of the embodiment of the invention shown in FIG. 1.

FIG. 1 illustrates a top-down perspective of the device, FIG. 2 illustrates a perspective from beneath the device 2 and FIG. 3 illustrates a side cross sectional view of the device 2 shown in FIGS. 1 and 2.

Referring to FIGS. 1 and 2 the device 2 includes a body 4 which is substantially elliptical or oval in shape. As can be seen from FIG. 3 the body 4 curves along its longitudinal axis. The body 4 also curves along its lateral axis. The arcuate curvature forms a device which is particularly suitable for articular cartilage repair (such as of the medial femoral condyle).

As can be seen in FIG. 2, the bottom surface of the body 4 includes anchoring elements 6, in the form of five anchoring elements 6a, 6b, 6c, 6d and 6e. Elements 6a-6e extend in a substantially cruciform arrangement from the bottom surface of the body 4, as shown in FIG. 2. The anchoring elements 6a-6e are substantially cylindrical, as shown in FIGS. 2 and 3. The body 4 and the anchoring elements 6a-6e are formed from a regenerated silk fibroin hydrogel, and the anchoring elements 6a-6e are formed integrally with the body 4 and from the same silk fibroin hydrogel material. Thus there is no separate join or connection between the anchoring elements 6 and the body 4.

The body 4 of the device 2 includes a fibre network in the form of a fibre layer 8. The fibre layer 8 includes lateral and longitudinal fibres extending in a single layer across the full length and width of the body 4. In the embodiment shown in FIGS. 1-3 the fibre layer 8 extends adjacent to the bottom surface of the body 4, as shown in FIG. 3. In this configuration, the fibre layer 8 also extends across the junction between the anchoring elements 6a-6e and the body 4.

Each of the anchoring elements 6a-6e also includes a fibre layer 10. The fibre layer 10 is a single layer of longitudinal and lateral fibres extending across the full cross sectional area of the anchoring elements 6a-6e, as shown in FIG. 2. The fibre layer 10 of each anchoring element 6a-6e is located towards and close to the free, distal end of each of the anchoring elements 6a-6e. The fibre layers 8 and 10 consist of silk fibres and each fibre layer 8, 10 consists of woven fibres which form a fibre mesh, as shown in FIGS. 1 and 2. The hydrogel of the body 4 and anchoring elements 6a-6e infiltrate the spaces between the fibres of the fibre layers 8, 10, and also completely surrounds the body 4 and anchoring elements 6a-6e.

As shown in FIG. 3, the fibre layer 10 of the anchoring element 6a-6e and the fibre layer 8 of the body 4 are connected via threads 12 which extend longitudinally through the anchoring elements 6a-6e. The threads 12 are stitched to the fibre layers 8 and 10.

The silk fibroin hydrogel material of the body 4 and anchoring elements 6a-6e is also cross-linked. Cross-linking can be achieved, for example by hydrogen bonding with a 30-70% v/v ethanol treatment. The cross-linked hydrogel material of the body 4 and anchoring element 6a-6e is relatively stiff. The fibre layers 8, 10 of the body 4 and anchoring element 6a-6e respectively provide structural support for the device 2 but also enable anchorage of biological material such as cells, growth factors etc to infiltrate and colonise the device 2 during use. The threads 12 provide further structural support for the anchoring elements 6a-6e, and the threads 12 extending between, and stitched to, the fibre layers 8, 10 ensure the fibre layers 8, 10 do not migrate away from each other, and are therefore more readily retained in the optimised position within the device 2.

The device 2 of the embodiment shown in FIGS. 1-3 is useful as a device for the repair of articular cartilage. It will be readily understood that the device 2 could be provided in many different shapes, for use in the repair, augmentation or replacement of other tissue, especially cartilage, such as meniscal cartilage, intervertebral discs and the like.

In use, the device 2 may be used to repair damaged articular cartilage in the following manner. Firstly, the damaged cartilage may be removed by a practitioner resulting in a hole within the articular cartilage, revealing the bone beneath. Five holes are then drilled in the bone, corresponding to the positions of the anchoring elements 6a-6e of the device 2, having a depth substantially identical to, or longer than, the length of the anchoring elements 6a-6e. After the holes have been drilled into the bone, the device 2 may be trimmed such that the body 4 mimics the shape and contours of the cartilage that it is intended to replace. In particular, the body 4 of the device 2 may be trimmed to conform to the edges of the hole formed in the cartilage, in order to fill said hole. In this configuration the anchoring elements 6a-6e are inserted into the holes in the bone. Alternatively, the lesion into which the device 2 will be implanted, may be further shaped to ensure that the device 2 fits into the lesion. The curvature of the back side of the device 2 can be tailored to match the curvature of the back of the lesion into which the device 2 is inserted, which spares the subchondral bone from damage or manipulation.

If desired, further bone anchors may be used, such as pins or bolts drilled through the device 2 and into the underlying bone of the articular cartilage. These further bone anchors may be bioresorbable or bioabsorable so that they may be used for initial fixation of the device 2, and are thereafter resorbed or absorbed.

The use of anchoring elements 6a-6e, which are integral with the body 4 and made from the same hydrogel material enables a single unitary device to be formed, with minimal internal weakness and an optimal ability to anchor securely to the bone and cartilage. In addition, the fibre layers 8, 10 and threads 12 provide excellent resistance to the hydrogel in the anchoring elements 6a-6e collapsing, warping or otherwise shrinking over time.

In other embodiments of the device 2 shown in FIGS. 1-3 there may be multiple fibre layers 8 in the body 4, stacked on top of each other. This further increases the stability and stiffness of the device 2. In yet further embodiments, the fibre layers 8, 10 include much thicker fibres, such that a single layer may substantially fill at least 25, 50% or more of the volume of the body 4 and anchoring elements 6a-6e. There may be multiple stacked fibres layers 8,10 which may serve to create a 3D fibre layer mat.

Compared to similar implantable tissue repair devices, which include separate and connected means to anchor the devices to tissue such as bone or cartilage (such as pins and bolts), the device 2 shown in FIGS. 1-3 includes many advantages including: ease of manufacture (e.g. the device 2 of the embodiment of FIGS. 1-3 can be manufactured in a single gelling and moulding process with no need to adhere different parts of a device together); the ability for the anchoring elements to match the material of the body of the device to ensure maximum biocompatibility; the ability to include a fibre network within the anchoring elements and therefore provide the anchoring elements with a fibre matrix for the subsequent infiltration of cells, growth factors etc from the surrounding tissue; and the ability to tailor the anchoring elements, size and shape, post-formation of the device 2, if required, in order to enable optimal securement to a tissue.

Figure 4:
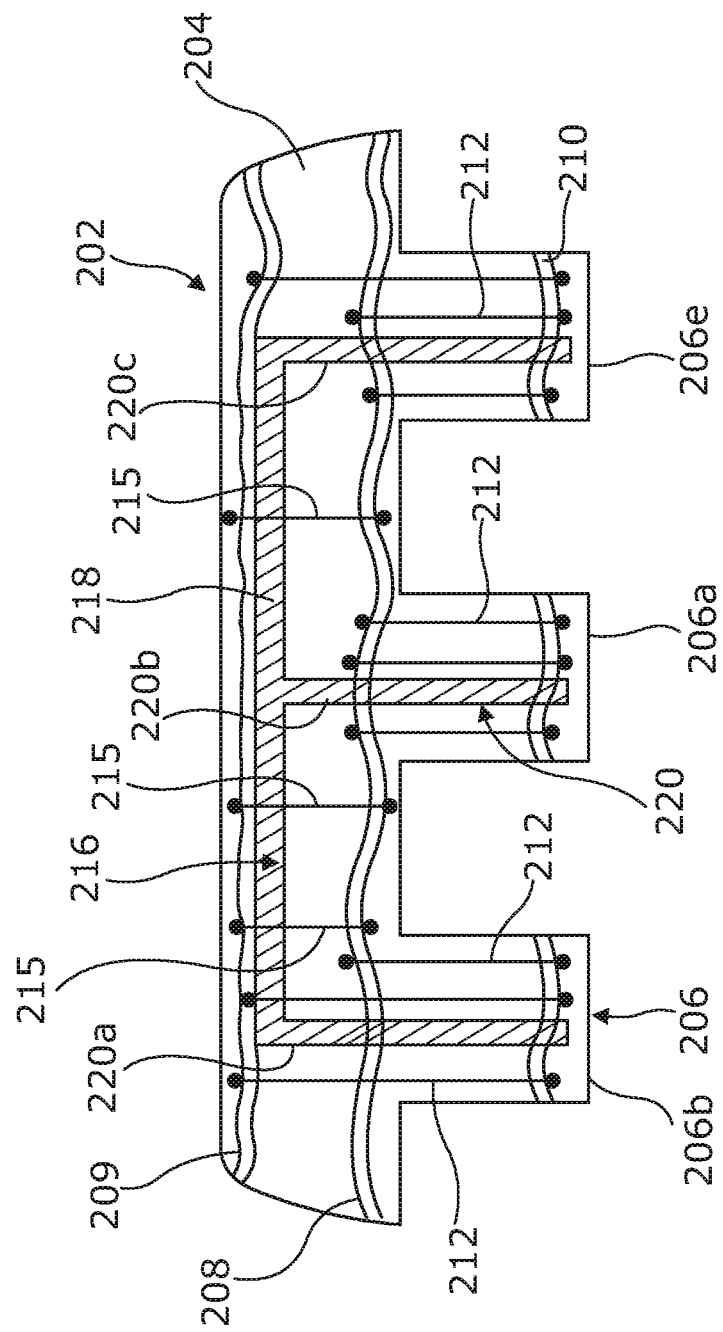
FIG. 4 illustrates a cross-sectional view from the side an embodiment of an implantable tissue repair device of the second aspect of the invention.

Turning now to FIG. 4, an embodiment of a device 202 of the invention is shown in a cross-sectional view. The device 202 is similar to the device 2 described hereinabove for FIGS. 1-3. The device 202 comprises an oval/elliptical body 204 from which project five anchoring elements 206, of which three anchoring elements 206a, 206b, 206e are shown in cross section. The body 204 is shown to have a relatively flat lower surface and upper surface, but in alternative embodiments may be contoured, such as having a convex upper surface and concave lower surface, for example. The anchoring elements 206 are in the same cruciform configuration as the anchoring elements 6 of the device 2 of FIGS. 1-3. The body includes a fibre network in the form of a fibre layer 208, and the anchoring elements include a fibre layer 210. The fibre layers 208 and 210 are identical to those described hereinabove in relation to the embodiment of the device 202 shown in FIGS. 1-3, and are located in the same positions within the device 202. In alternative embodiments fibre layer 208 may be omitted. The anchoring elements 206 also include threads 212 extending longitudinally between the fibre layer 208 of the body 204 and the fibre layer 210 of the anchoring element 206. The body 204 and anchoring elements 206 are integrally formed from the same silk fibroin hydrogel material; and the fibre layers 208, 210 comprise silk fibres, as described hereinabove.

The device 202 of FIG. 4 includes a rigid framework 216 formed from titanium or a porous ceramic material comprising zirconium oxide. The rigid framework 216 includes a number of frame members. A hollow rectangular frame member 218 extends through the body 204 of the device 202, as shown in FIG. 4. The rectangular frame member 218 also includes internal struts (not shown), extending between opposite sides of the frame 218. Rigid frame members 220 extend from the frame member 218 and struts into each of the anchoring elements 206. FIG. 4 illustrates frame members 220a, 220b, 220c extending into anchoring elements 206a, 206b, 206e. It will be appreciated that further frame members 220 will extend into the other anchoring elements 206 of the device 202. The rigid framework 216 therefore provides frame members 218, 220 extending through both the body 204 and the anchoring elements 206 of the device 202.

The body 204 also includes a second fibre layer 209 on top of the rigid frame 218 of the framework 216. The fibre layer 209 is identical in shape and configuration to the fibre layer 208 and extends across the whole length and breadth of the body 204. The fibre layer 209 is stitched to the frame 218 and to the fibre layer 208 via threads 215, as shown in FIG. 4. In this configuration, the fibre layer 209 and fibre layer 208, being directly or indirectly stitched to the frame 218, ensures that the rigid framework 216 cannot move substantially within the body 204. Conversely, as the fibre layers 208 and 209 are stitched to the rigid framework 216, the fibre layers 208, 209 are also prevented from substantially moving within the body 204. This configuration, shown in FIG. 4, provides the device 202 with increased structural stability and strength, and ensures that post-implantation, the device 202 does not wrinkle, flex or otherwise contort.

Use of the device 202 is substantially identical to the use described hereinabove for the device 2 of FIGS. 1-3, and the anchoring elements 206 of the device 202 are inserted into holes drilled into bone as described above.

The devices 2, 202 of FIGS. 1 to 4 may be manufactured by preparing a silk fibroin hydrogel precursor solution in a mould; incorporating the various fibre layers of the devices 2, 202 in the mould; in the case of the device 202 of the embodiment shown in FIG. 4, a rigid framework is also incorporated within the hydrogel precursor solution in the mould; the hydrogel precursor solution is then gelled using any suitable technique (such as addition of an acid) at which point the body and anchoring elements of the devices 2, 202 form the stiff, resilient hydrogel within the mould, and the resultant devices 2, 202 may then be removed from the mould. Optionally, the resultant hydrogels may be subjected to one or more steps of freezing and thawing in order to introduce pores into the hydrogel. It is particularly desirable to undertake one or more cycles of freezing and thawing in order to introduce pores into the hydrogel in order for optimal infiltration of biological material into the device when implanted into a tissue. In particular, one or more freezing and thawing cycles is useful to introduce pores into the anchoring elements 6, 206 of the devices 2, 202, and at least the lower surface of the bodies 4, 204.

The various threads 12, 212, 215 are stitched in place on the fibre layers and rigid framework before the fibre layers and rigid framework are incorporated into the hydrogel precursor solution. The devices 2, 202 may be prepared using an apparatus as shown in FIGS. 5 to 10.

Figure 5:
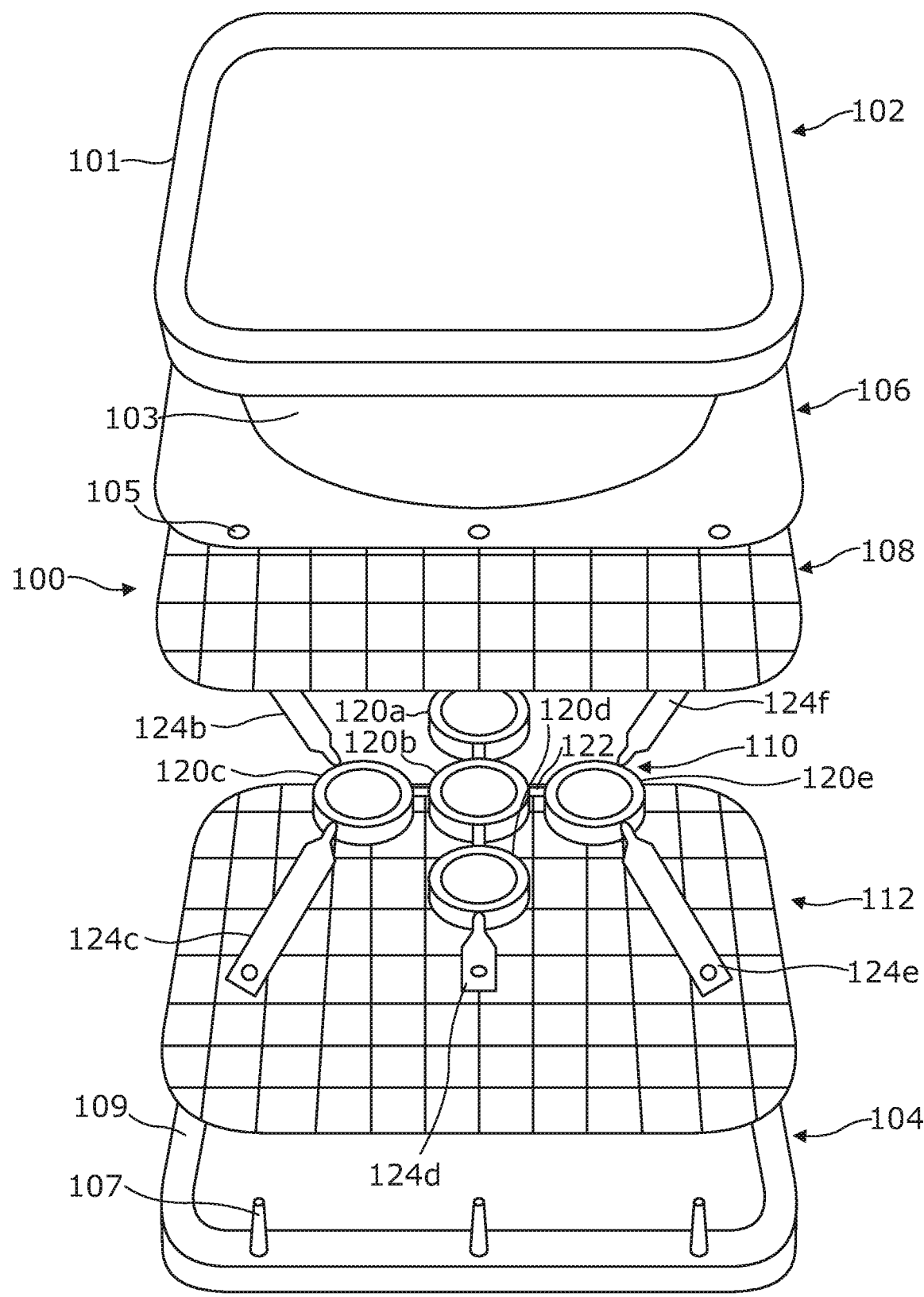
FIG. 5 illustrates an exploded view of a frame and central mould part used to manufacture embodiments of the devices of the invention with upper and lower fibre layers incorporated therein.
Figure 6:
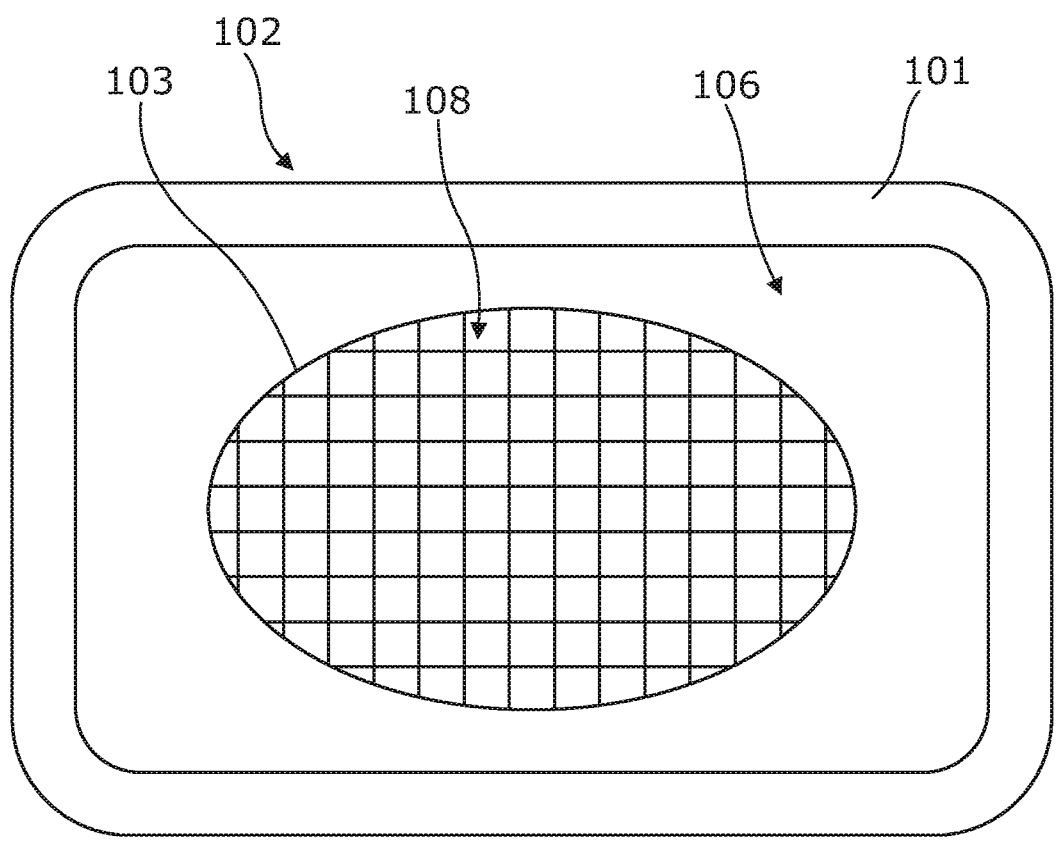
FIG. 6 is a top-down view of the frame and central mould when assembled.
Figure 7:
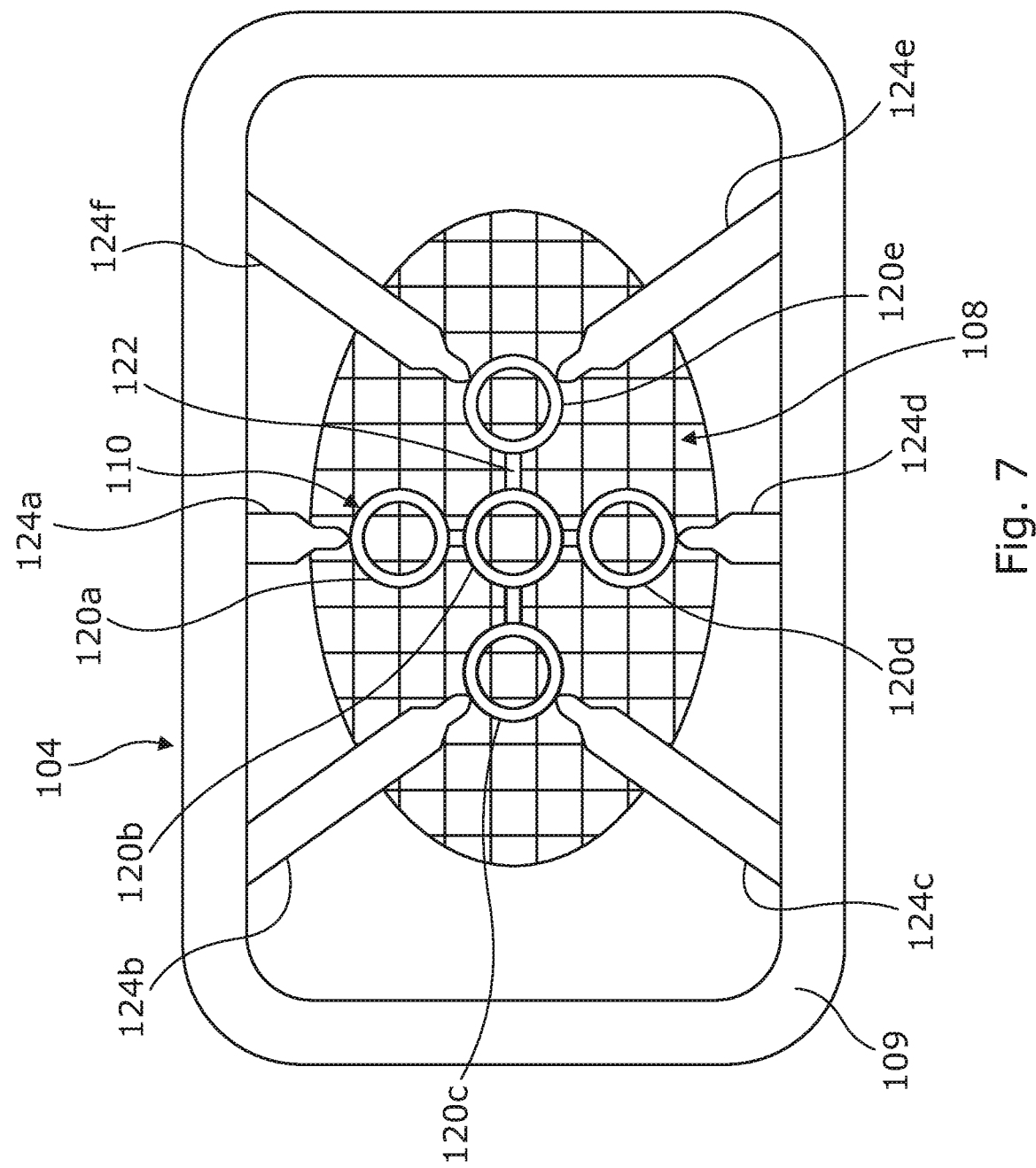
FIG. 7 is a bottom-up view of the frame and central mould when assembled, but without the lower fibre layer.
Figure 8:
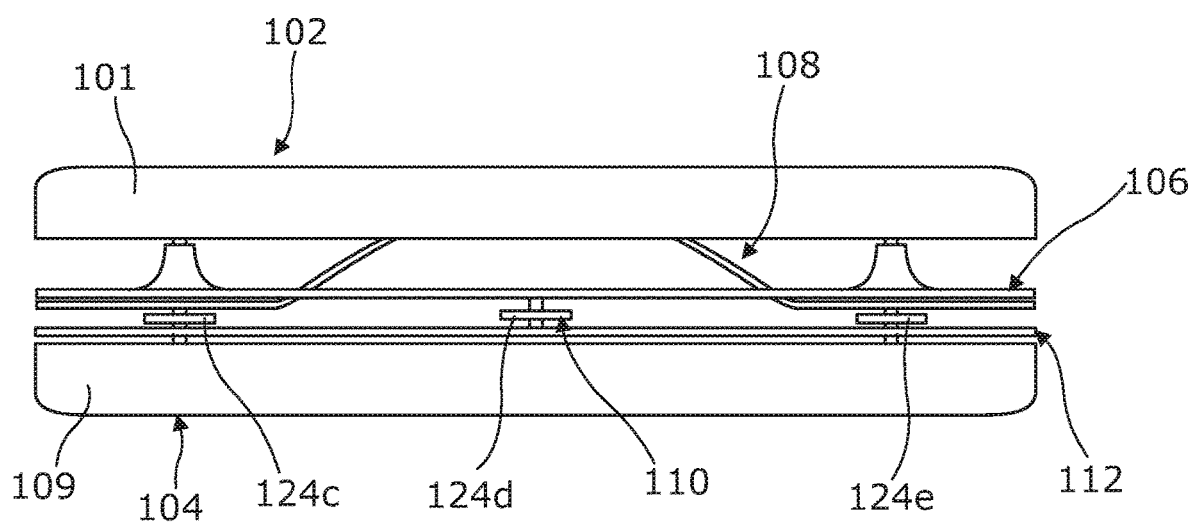
FIG. 8 is a side view of the frame and central mould of FIG. 5 when assembled.
Figure 9:
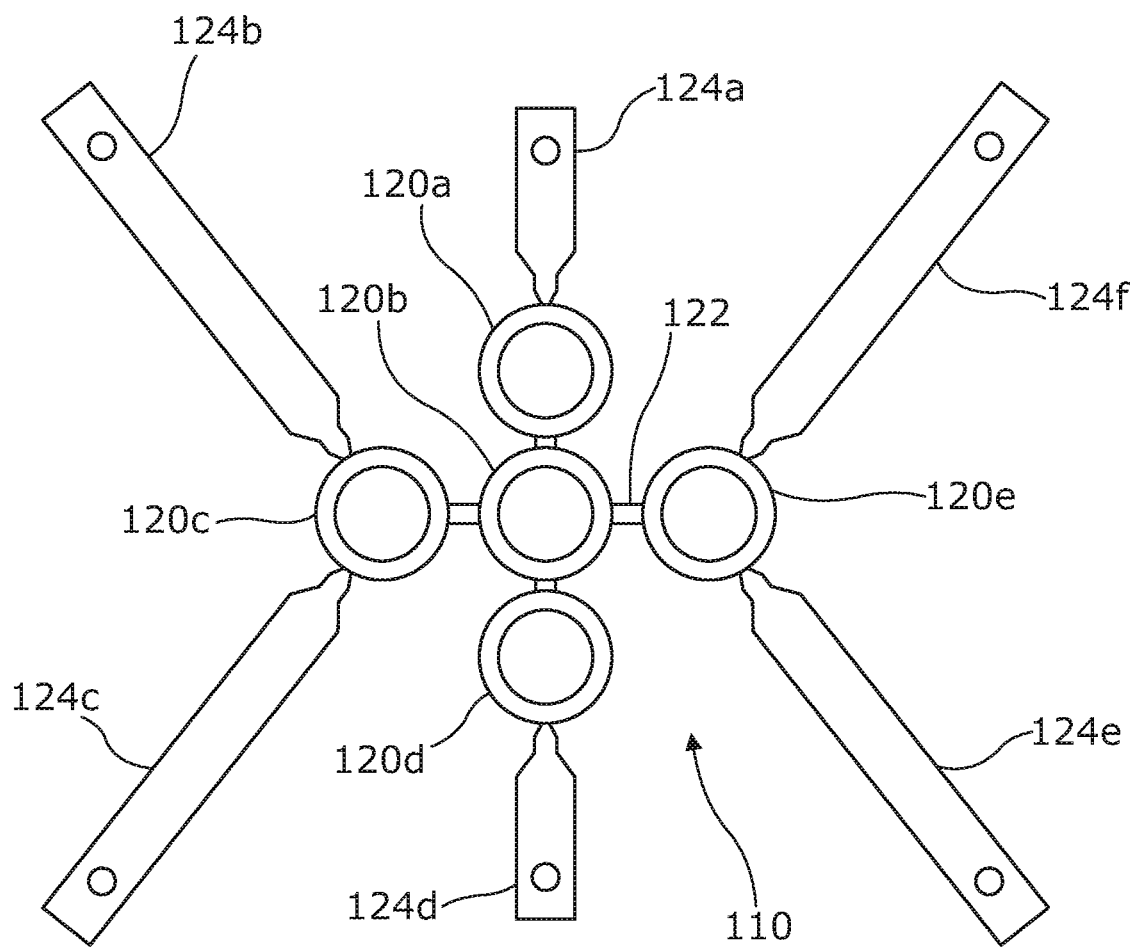
FIG. 9 is a top-down view of an anchoring elements former used in the frame of FIGS. 5 to 8.

FIGS. 5-9 illustrate a carriage 100 used in the formation of the devices 2, 202. FIG. 5 illustrates an exploded view of the carriage 100; whilst FIG. 6 illustrates a top down view of the complete carriage 100; FIG. 7 illustrates a bottom-up view of the carriage 100; FIG. 8 illustrates a side view of the carriage 100 and FIG. 9 illustrates an anchor element forming device 110 used in the carriage 100. As shown in FIG. 5, the carriage 100 includes an upper frame member 102 and lower frame member 104 which together form a frame of the carriage.

The upper frame member 102 and lower frame member 104 include rectangular frames 101 and 109 respectively, each bounding a cavity. The lower frame member 104 includes connection pins 107. Between the upper frame member 102 and lower frame member 104, from top to bottom are: a central mould part 106 and an anchoring element former 110.

Also shown in FIG. 5 are fibre layers 108 and 112 which correspond to the fibre layers 8, 12 and 208, 212 of the embodiment shown in FIGS. 1-4. The fibre layer 108 is located between the central mould part 106 and the anchoring element former 110; whilst the fibre layer 112 is located below the anchor element former 110.

The central mould part 106 comprises a central aperture 103 around which extends a frame having pin apertures 105.

The anchoring element former 110 includes five anchoring element moulds 120a-120e (corresponding to the positions of the anchoring elements 6, 206 of the devices 2, 202). The anchoring element moulds 120a-120f are joined by spurs 122 and arranged in a cruciform shape. Extending from the outer most anchoring element moulds 120a, 120c, 120d, 120e, are connection arms 124a-124f as particularly shown in FIGS. 7 and 9. The arms 124a-f include pin holes which, when the carriage is formed, align with the pins 107 of the lower frame member 104. In use, the various parts of the carriage 100 are joined together to form a carriage 100 as shown in FIG. 8. When joined, the pins 107 of the lower frame member 104 extend through the arms 124a-124f of the anchoring element former 110, and into the central mould 106 part via pin apertures 105, and finally into apertures in the upper frame member 102 (not shown). This ensures that the various parts of the carriage 100 are firmly joined together.

As shown in FIG. 8, when the carriage 100 is completed, the fibre layer 112 is located beneath the anchoring element former 110, such that it covers the underside of the anchoring element moulds 120a-120e. Above the anchoring element moulds 120a-120e is the second fibre layer 108 which extends above the upper surface of the anchoring element moulds 120a-120e. The anchoring element former 110 is configured such that when the carriage is joined, it urges the upper fibre layer 108 through the central aperture 103 of the central mould part 106, as shown in FIG. 8. In addition the anchoring element former 110 also extends through the central aperture 103 of the central mould part 106.

The carriage 100 can then be used in a final mould to manufacture the devices 2, 202 of the embodiments shown in FIGS. 1-4.

Referring to the embodiment of the device 2 shown in FIGS. 1-3, the device 2 is manufactured as follows.

Figure 10:
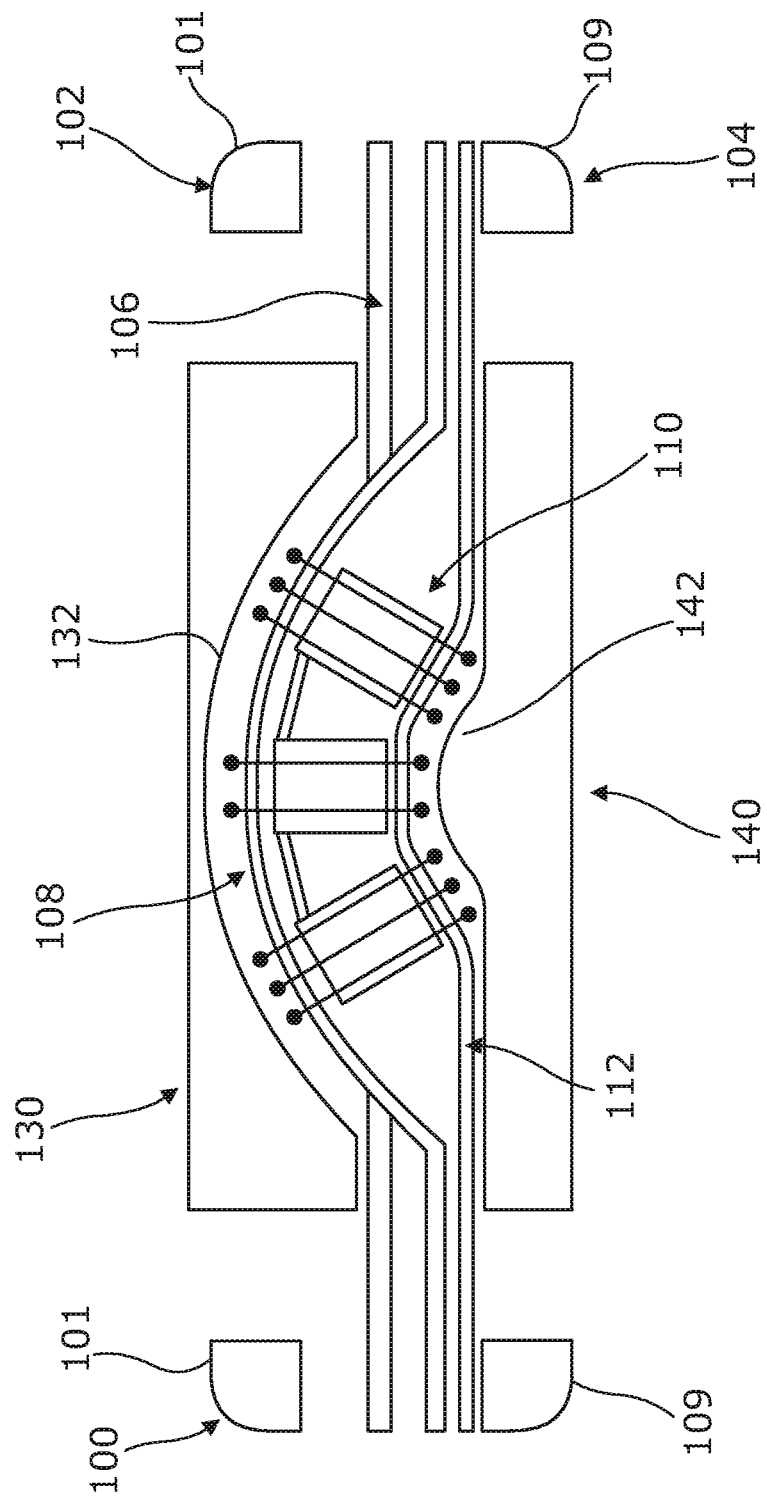
FIG. 10 is a side cross-sectional view of the frame of FIGS. 5 to 9 with connected mould parts of an embodiment of an apparatus of the invention.
Figure 11:
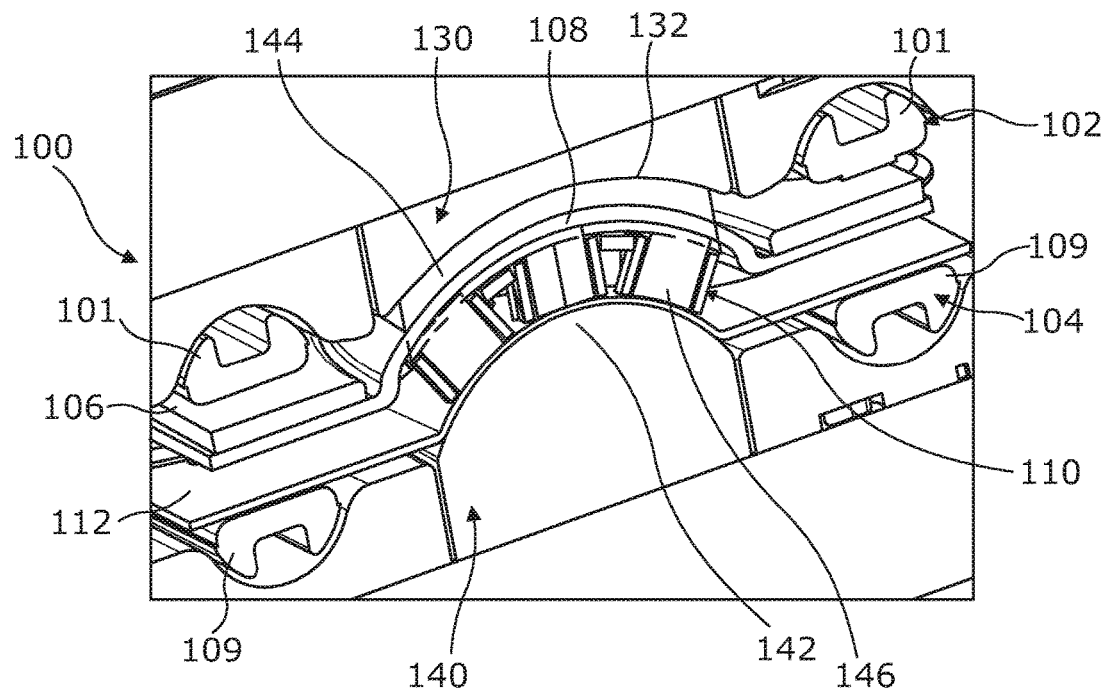
FIG. 11 is a side view of the apparatus of the FIG. 10.

The carriage 100 is clamped between two further mould parts as shown in FIGS. 10 and 11. FIG. 10 illustrates a cross sectional view through the carriage 100, when clamped between further upper mould part 130 and lower mould part 140. The final mould consists of the upper mould part 130, central mould part 106 and lower mould part 140. The lower mould part 140 consists of a mould plate having a convex protrusion 142 which extends to help urge the anchoring element former 110 through the central aperture 103 of the central mould part 106. This convex portion 142 also urges the lower fibre layer 112 onto the free, distal end of the anchoring element former 110. The anchoring element former 110 also urges the upper fibre layer 108 through the central aperture 103 of the central mould part 106. The upper mould part 130 consists of a plate with a concave configuration, which, as can be seen in FIG. 10, matches the contours of the fibre layer 108, anchoring element former 110 and fibre layer 112 as they protrude from the central aperture 103 of the central mould part 106.

The upper mould part 130 is lowered onto the central mould part 106 such that a gap exists between the surface of the concave portion 132 of the upper mould part 130 and the upper fibre layer 108. In a similar manner, the lower mould part 140, having ensured that the anchoring element former 110 is moved to the correct configuration. In alternative embodiments the lower mould part 140 may be withdrawn slightly to provide a thin gap between the lower fibre layer 112 and the convex portion 142 of the mould part 140.

It is to be noted that in FIG. 10, threads have been stitched between the lower fibre layer 112 and upper fibre layer 108. Once the elements of the carriage 100 and upper and lower mould parts 130, 140 are all in position, the carriage and mould parts may be inserted into a dialysis bag (necessary only if the resultant hydrogel will be formed of silk fibroin), then a hydrogel precursor solution is then injected between the upper mould part 130 and lower mould part 140. In some embodiments, the entire carriage 100 and upper and lower mould parts 130, 140 are submerged in a container of hydrogel precursor solution. The hydrogel precursor solution infiltrates the space between the concave portion 132 of the upper mould part 130 and the convex portion 142 of the lower mould part 140 and fills the gap therebetween, including filling the interior of the anchoring element former 110. The hydrogel precursor solution may then be gelled by any suitable method (such as addition of an acid), in order to form the hydrogel of the devices 2, 202.

It can be seen from FIG. 11 that hydrogel 144 will form between the upper mould part 130 and lower mould part 140 in the shape of the body 4, 204 of the devices 2, 202, and will also form solid hydrogel 146 within the anchoring element former 110 to provide the integral anchoring elements 6, 206 of the devices 2, 202. On completion of gelation the upper mould part 130 and lower mould part 140 may be withdrawn, and the solid hydrogel body cut from the central mould 106 part in a shape substantially matching the contours of the central mould aperture 103. The ends of the anchoring elements 6, 206 are also cut free, in order to ensure that anchoring elements can be withdrawn through the anchoring element former 110. The body of the device 2, 202 may then be withdrawn. Upon withdrawal, the anchoring elements located within the anchoring element former 110 will also be withdrawn therefrom, and the corresponding parts of the lower fibre layer 112 within the anchoring elements 6, 206 will be withdrawn through the anchoring element former 110. The threads, stitched between the lower fibre layer 112 and upper fibre layer 108 ensure that the lower fibre layer 112 does not delaminate from the anchoring elements 6, 206 as the devices 2, 202 are withdrawn from the central mould part 106. Before (or after) being withdrawn from the mould, the devices 2, 202 may undergo one or more cycles of freezing and thawing in order to introduce pores into the bodies and anchoring elements 6, 206 of the devices 2,202.

For the manufacture of the device 202 of the second embodiment of the invention, the rigid framework 216 may be inserted through the central aperture 103 of the central mould part 106 before the upper frame 102 is clamped onto the central mould part 106. The rigid framework 216 will penetrate through the upper fibre layer 108, and the legs 220 of the rigid framework 216 will extend through the cylinders 120 of the anchoring element former 110, and protrude slightly through the lower fibre layer 112. A top most fibre layer (not shown in FIG. 10) may then be placed on top of the rigid framework 216, to provide the fibre layer 209 shown in FIG. 4. The top most fibre layer may be stitched to the upper fibre layer 208 using threads, as hereinbefore described and may be stitched to the rigid framework 216. The carriage 100 may then be fully clamped together as described above; the carriage and upper mould part 130 and lower mould part 140 brought together; and the device 202 formed in the same manner as described above.

Figure 12:
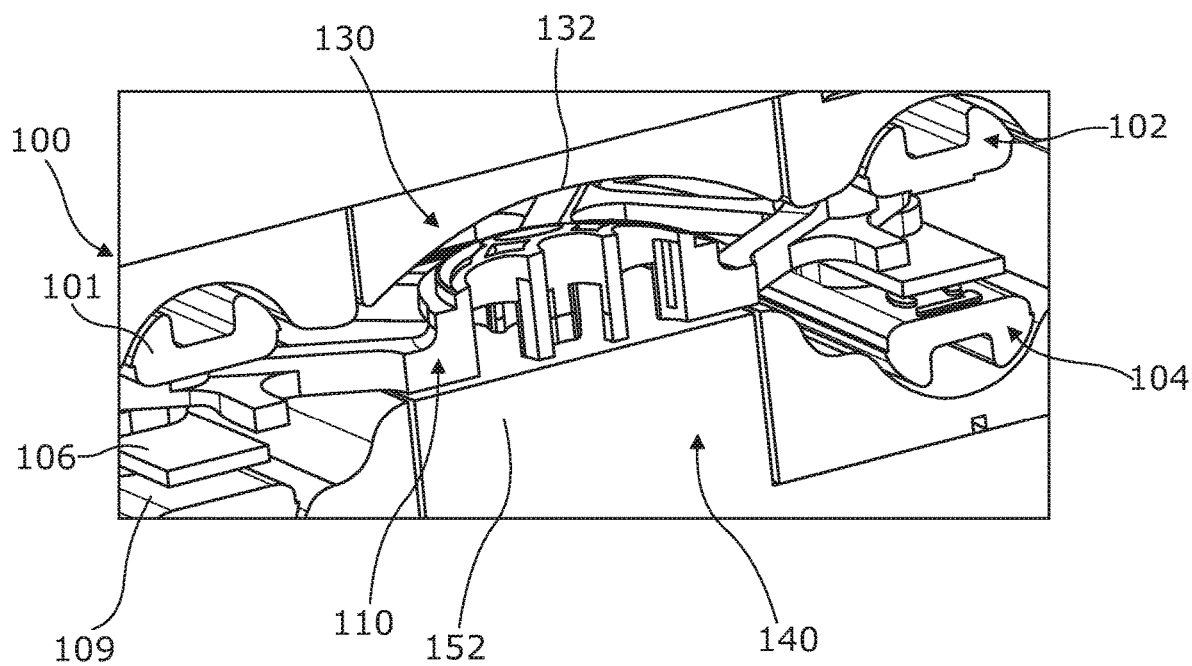
FIG. 12 is a side view of another embodiment of an apparatus of the invention.

FIG. 12 illustrates a second embodiment of an apparatus of the invention used to manufacture devices of the invention. The apparatus is similar to that described for the example of FIGS. 10 and 11, and like numerals represent like components. The apparatus shown in FIG. 12 does not show the fibre layers 108, 112, but they can be inserted into the carriage 100 as described hereinabove in reference to FIGS. 10 and 11. The primary differences between the apparatus of FIG. 12 and that of FIGS. 10 and 11 is in the shape of the anchoring element former 110 and the lower mould part 140. In the embodiment of FIG. 12 the upper surface 152 of the lower mould part 140 is substantially flat and the anchoring element former 110 is domed such that the upper surface creates a convex shape, which will correspond to a concave back surface of the body of the device formed in the apparatus. The flat upper surface 152 of the lower mould 140 pushes the anchoring element former 110 substantially through the central aperture of the central mould part 106. The anchoring element former 110 then serves to form the anchoring elements and the shape of the back surface of the body of the device, in use.

Figure 13:
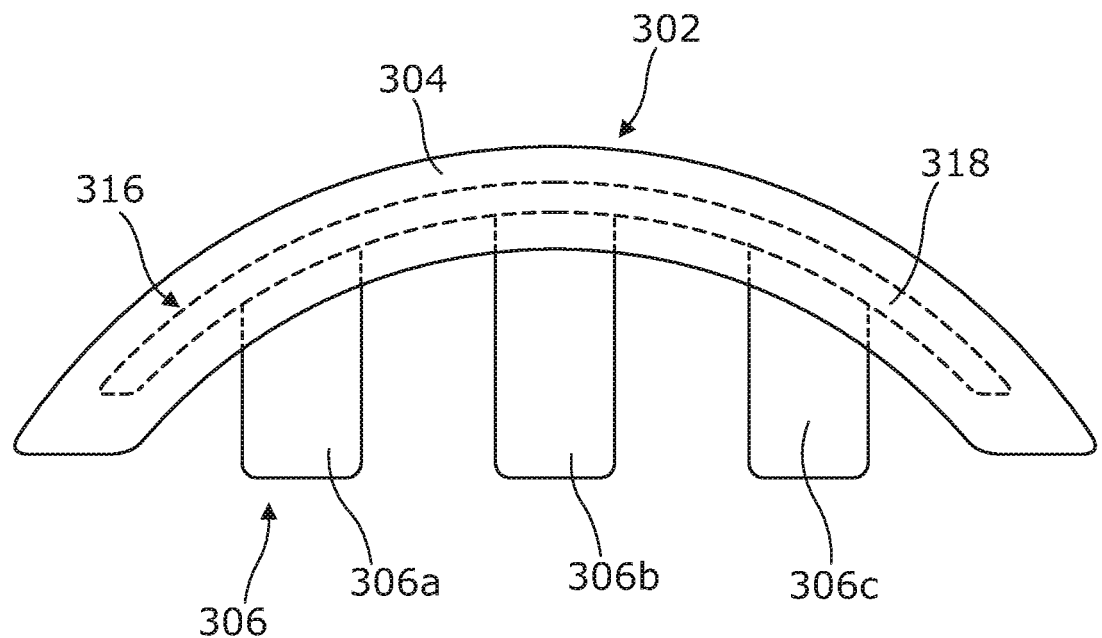
FIG. 13 is a side view of a second embodiment of an implantable repair device of the second aspect of the invention.

FIG. 13 illustrates a side view of a device 302 of the second aspect of the invention. The device 302 includes a body 304 in which is located a rigid support in the form of a framework 316 (illustrated in dotted lines to show that it is internal in the body 304) The body comprises a silk fibroin hydrogel, as described above for the embodiment illustrated in FIG. 4. The rigid framework 316 is formed of a porous ceramic zirconium oxide material which is porous. The framework 316 includes plate 318 extending across a substantial portion of the body 304. The framework 316 also includes a number of anchoring elements 306, of which three elements 306a, 306b and 306c are shown in side view. The anchoring elements are also formed from zirconium oxide and are integrally formed with the plate 318. The anchoring elements project from the body 304 of the device 302, and are not coated in hydrogel. Thus, the anchoring elements 306 projecting from the body 304 have outer surfaces of porous zirconium oxide. The porous outer surfaces enable ready infiltration of biological matter when the anchoring elements 306 are inserted into apertures in a tissue such as bone or cartilage, after anchoring the device 302 to the tissue. Although the device 302 shown in FIG. 13 does not show fibres networks within the body, these may be incorporated as described above for the embodiment of FIG. 4, and may include at least one fibre network above the plate 318 and at least one fibre network within the anchoring elements 306, and the fibre networks may be stitched together via threads, thereby bounding the plate 318 and anchoring elements 306 therebetween.

Figure 14:
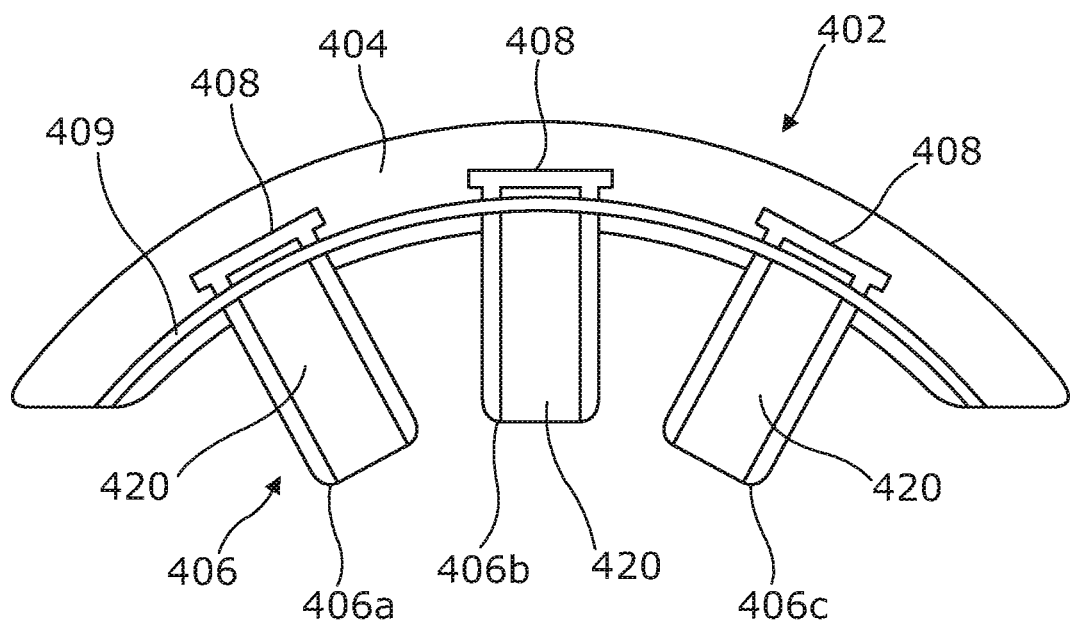
FIG. 14 is a side cross-sectional view of a third embodiment of an implantable repair device of the second aspect of the invention.

FIG. 14 is a side cross-sectional view through a third embodiment of a device 402 of the second aspect of the invention. The device 402 comprises a silk fibroin hydrogel body 404. The body 404 includes a fibre mesh layer 409 which extends through the body adjacent to the lower surface thereof. The fibre mesh layer 409 includes apertures, through which a number of rigid titanium anchoring elements 406 project. Three anchoring elements 406a, 406b and 406c are shown in cross section. The anchoring elements 406 are hollow titanium pegs and during formation of the anchoring elements 406, hydrogel fills the cavities 420 of the anchoring elements 406. The hydrogel in the cavities is in communication with the hydrogel of the body 404 via an annular upper end 408 of the anchoring elements 406 within the body. The hydrogel of the cavities 420 is also exposed at the open distal ends of the anchoring elements 406. As the hydrogel is exposed at the end of the anchoring elements 406, when the anchoring elements 406 anchor the device in a tissue, biological material such as blood, plasma, bone marrow etc. may infiltrate the pores of the hydrogel.

Figure 15:
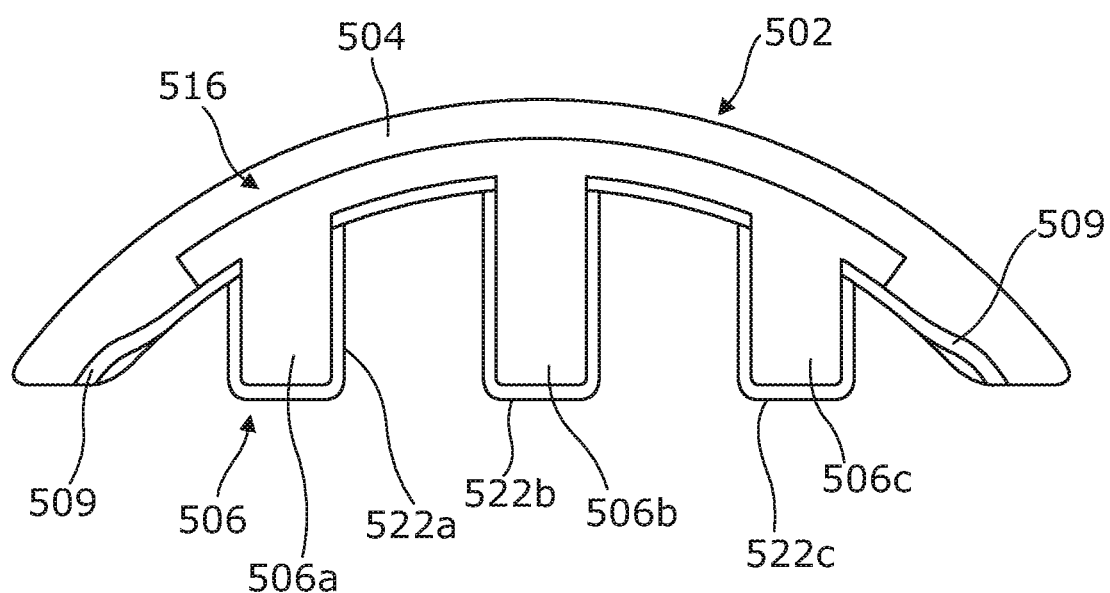
FIG. 15 is a side cross-sectional view of a fourth embodiment of an implantable repair device of the second aspect of the invention

FIG. 15 illustrates a side sectional view of a fourth embodiment of a device 502 of the second aspect of the invention. The device 502 is similar to that shown in FIG. 13 and includes a hydrogel body 504 in which is located a rigid support in the form a titanium framework 516. The framework 516 includes anchoring elements 506 which project out from the back surface of the body 504. The anchoring elements 506 are coated in a sacrificial wax layer 522a, 522b, 522c, so that during storage, the outer surfaces of the anchoring elements 506 are protected from contact with any material. When it is desired to expose the outer surfaces of the anchoring elements 506, the wax coating 522a, 522b, 522c may be removed. The body 504 also includes a fibre mesh layer 509 extending therethrough, at the junction between the body 504 and the anchoring elements 506. The mesh layer 509 is penetrated by the anchoring elements 506 and thereby prevents the framework 516 from being pulled through the bottom surface of the body 504, during use of the device 502.

Figure 16:
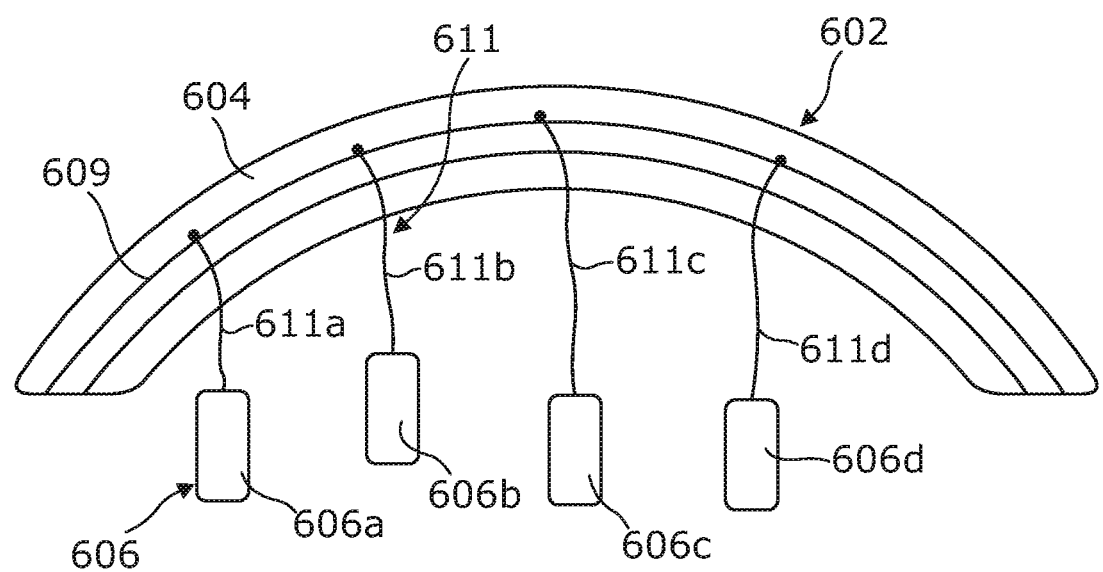
FIG. 16 illustrates a side cross-sectional view through a further embodiment of an implantable repair device of the invention.

FIG. 16 illustrates a side cross-sectional view through a further embodiment of an implantable repair device 602 of the invention. The device 602 comprises a silk fibroin hydrogel body 604 through which extends a fibre mesh layer 609. The fibre mesh layer 609 is connected to a number of anchoring elements 606 which are located external to and spaced apart from the body 604 via intermediate connections in the form of nylon sutures 611 stitched to the fibre mesh network 609 and extending into and secured in the anchoring elements 606. In the embodiment shown in FIG. 16, there are four anchoring elements 606a-d connected to the fibre mesh 609 at spaced apart intervals, via sutures 611a-611d.

Figure 17:
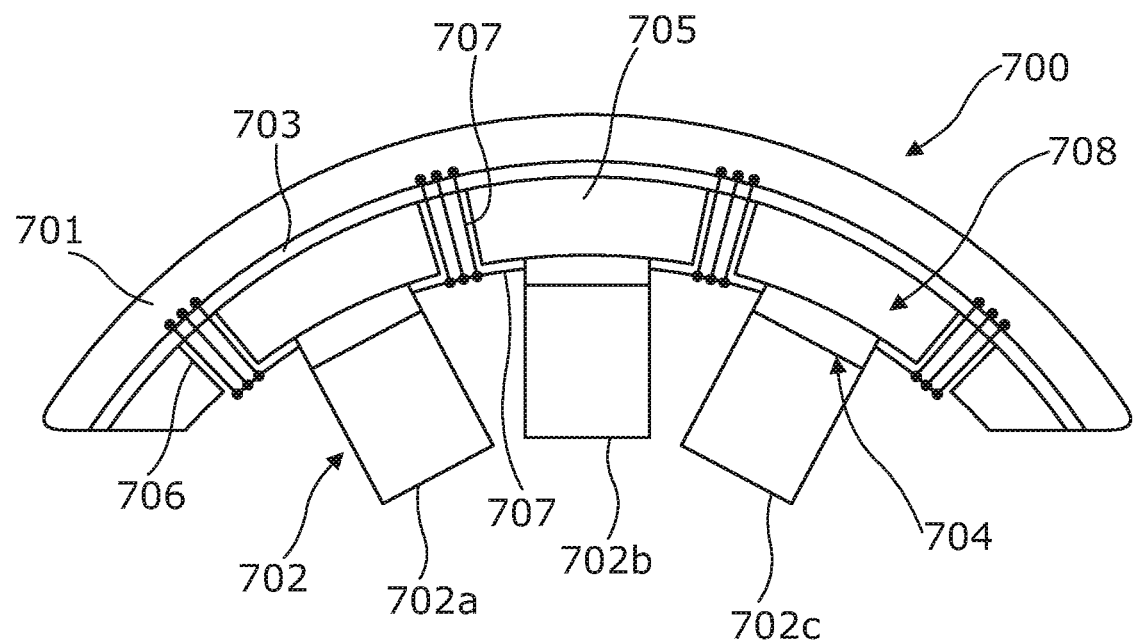
FIG. 17 is a side cross-sectional view of a fifth embodiment of an implantable repair device of the second aspect of the invention.

FIG. 17 is a side cross-sectional view of a sixth embodiment of an implantable repair device 700 of the second aspect of the invention. The device 700 comprises a silk fibroin hydrogel body 701 and a rigid support (in the form of a rigid framework 708) embedded within the silk fibroin hydrogel body 701. The rigid framework 708 comprises a porous Tritanium® plate 705 and a plurality of anchoring elements 702, three of which 702a-c are shown in cross-section. The anchoring elements 702 are integral with the plate 705 of the rigid framework 708, are not coated in hydrogel, and are formed mainly from porous Tritanium®, but further comprise a band of solid titanium 704. The bands of solid titanium 704 span the entire cross-sectional area of the anchoring elements 702 (i.e. the bands are circular so that they span the entire circular cross-section of the cylindrical anchoring elements), and therefore completely separate the porous Tritanium® plate 705 of the rigid framework 708 and the porous Tritanium® part of the anchoring elements 702. The bands 704 serve to prevent the seeping through of hydrogel from the body 705 into the porous Tritanium® part of the anchoring elements 702, which allows the pores in the anchoring elements 702 to remain substantially clean/unfilled and therefore to allow for more effective ingrowth of biological material into the porous anchoring elements 702 after implantation. This may be combined with masking/coating of the anchoring elements 702, for example with a sacrificial wax layer. The plate 705 of the rigid framework 708 includes an array of channels 706 (3 of which are shown) running therethrough. Therefore, the plate 705 is not segmented but is comprised of a single piece of Tritanium® with a number of channels 706 running through it. The device 402 further comprises a fibre mesh layer 703 connected to the top of the rigid plate 705. Threads 707 are stitched to/above the fibre mesh layer 703 and form a woven network which runs through the channels 706 in the rigid plate 705 and underneath the rigid plate 705. The threads 707 run around/between the anchoring elements 702, and may run in any direction along the bottom of the rigid plate 705, not just in the direction shown in FIG. 17. The threads 707 provide the implant with excellent support and secure the rigid support to the hydrogel body 701. The woven thread network which runs underneath the rigid plate 705 may be replaced or supplemented with a fibre layer below the rigid plate, substantially the same as the fibre layer of the device 502 of FIG. 15. The fibre layer beneath the rigid plate 705 may be stitched to the fibre layer 703 above the rigid plate 705 by threads, for example in substantially the same way as for devices 2 or 202 of FIGS. 3 and 4, respectively. The woven network of threads 707 may also run laterally and/or vertically around a side of the rigid plate 705, for example as described for the device 800 of FIG. 18 below.

Figure 18:
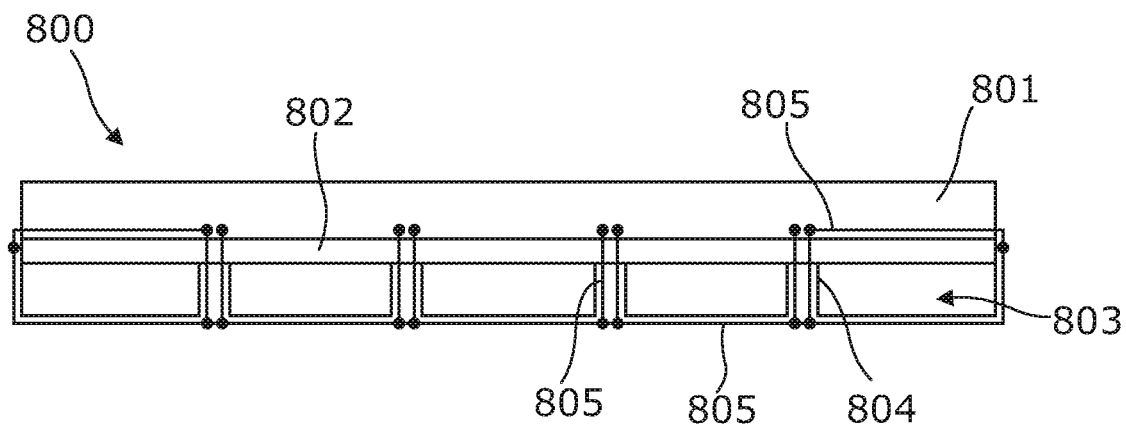
FIG. 18 is a side cross-sectional view of a sixth embodiment of an implantable repair device of the second aspect of the invention.

FIG. 18 is a side cross-sectional view of a sixth embodiment of an implantable repair device 800 of the second aspect of the invention. The device 800 is very similar to the device 700 of FIG. 17, and comprises a silk fibroin hydrogel body 801, an embedded rigid support in the form of a porous Tritanium® rigid plate 803, a fibre mesh layer 802 connected above the rigid plate 803, and threads 805 stitched to the fibre mesh layer 802 which form a woven thread network which runs through channels 804 in, and underneath, the rigid plate 803. However, the device 800 lacks anchoring elements, and the woven network of threads 805 additionally runs vertically around the side of the rigid plate 803, further supporting the body 801 to the rigid plate 803. The woven network of threads 805 may additionally run laterally around the side of the rigid plate 803, such that it runs around at least a portion of the perimeter of the device 800.

The above embodiments are described by way of example only. Many variations are possible without departing from the scope of the invention, as particularly defined in the appended claims.

The invention claimed is:
1. An implantable tissue repair device comprising;
a body comprising a biocompatible hydrogel; and
a plurality of tissue anchoring elements projecting from the body;
wherein the anchoring elements are integrally formed with the body and comprise the same biocompatible hydrogel as the body, and wherein the anchoring elements, in use, are arranged to enter apertures in a tissue and anchor the device to the tissue;
wherein the body of the device comprises at least one discrete layer of fibres on top of the anchoring elements and each anchoring element comprises at least one separate discrete layer of fibres located towards a free distal end thereof,
wherein said at least one separate discrete layer of fibres of the anchoring elements comprises a single layer of longitudinal and lateral fibres extending across the full cross-sectional area of the anchoring elements and the hydrogel of the anchoring elements infiltrates spaces between the fibres of the at least one layer of fibres of the anchoring elements, and
wherein the anchoring elements include at least one thread, stitched through the layer of fibres of the anchoring elements and which extends from the layer of fibres of the anchoring elements substantially parallel with a longitudinal axis of the anchoring elements and is stitched to at least one fibre layer of the body.
2. A device as claimed in claim 1, comprising a front surface and a back surface, and wherein the anchoring elements are located on the back surface, and project therefrom.
3. A device as claimed in claim 1, wherein the hydrogel comprises at least one material selected from the group consisting of silk fibroin, gelatin, fibrin, fibronectin, alginate, collagen, hyaluronic a acid, chondroitin sulphate, and derivatives thereof.
4. A device as claimed in claim 1, wherein at least part of the body and/or anchoring elements is porous.
5. A device as claimed in claim 4, wherein the porous part of the body and/or porous anchoring elements comprises at least 25% or more porosity by volume.
6. A device as claimed in claim 5, wherein the porous part of the body and/or porous anchoring elements comprises between 65% and 95% porosity by volume.
7. A device as claimed in claim 4, wherein the porous part of the body and/or anchoring elements comprises an open porous network.
8. A device as claimed in claim 1, wherein the hydrogel in the body and/or anchoring elements is cross-linked.
9. A device as claimed in claim 8, wherein the hydrogel is further cross-linked to the fibres of the fibre layer of the body and/or the anchoring elements.
10. A device as claimed in claim 1, wherein the body and/or anchoring elements comprise at least one porous surface.

11. A device as claimed in claim 10, wherein the body and/or anchoring elements is porous, and pores of the at least one porous surface communicate with pores within the body and/or anchoring elements.

12. A device as claimed in claim 10, wherein each porous surface of the at least one porous surface is mineralised.

13. A device as claimed in claim 1, wherein the anchoring elements have a length of approximately 75%, 65%, 50%, 33% or 25% of a thickness of the body.

* * * * *